(12) United States Patent
Kaye

(10) Patent No.: US 10,229,519 B2
(45) Date of Patent: Mar. 12, 2019

(54) METHODS FOR THE GRAPHICAL REPRESENTATION OF GENOMIC SEQUENCE DATA

(71) Applicant: The University of British Columbia, Vancouver (CA)

(72) Inventor: Alice Kaye, Burnaby (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 15/161,147

(22) Filed: May 20, 2016

(65) Prior Publication Data

US 2016/0342737 A1 Nov. 24, 2016

Related U.S. Application Data

(60) Provisional application No. 62/165,543, filed on May 22, 2015.

(51) Int. Cl.
*G06T 11/60* (2006.01)
*G06T 11/20* (2006.01)
(Continued)

(52) U.S. Cl.
CPC ............ *G06T 11/206* (2013.01); *G06F 19/18* (2013.01); *G06F 19/22* (2013.01)

(58) Field of Classification Search
CPC ........ G06T 11/206; G06F 19/18; G06F 19/20; G06F 19/22; G06F 19/24; G06F 19/26; G06F 19/16
(Continued)

(56) References Cited

U.S. PATENT DOCUMENTS 7,289,911 B1 * 10/2007 Rigney .................. G06F 19/28
702/19
9,063,914 B2    6/2015 Kural et al.
(Continued)

FOREIGN PATENT DOCUMENTS

WO    2015/123269 A1    8/2015

OTHER PUBLICATIONS

Raphael, Benjamin, Degui Zhi, Haixu Tang, and Pavel Pevzner. "A novel method for multiple alignment of sequences with repeated and shuffled elements." Genome Research 14, No. 11 (2004): 2336-2346.*

(Continued)

*Primary Examiner* — Sarah Lhymn
(74) *Attorney, Agent, or Firm* — Christensen O'Connor Johnson Kindness PLLC

(57) ABSTRACT

This disclosure provides a computational framework with related methods and systems to enhance the analysis of genomic information. More specifically, the disclosure provides for a graph-based reference genome framework, referred to as a GNOmics Graph Model (GGM), which represents genomic sequence information in edges with nodes representing transitions between edges. The disclosed GGM framework can represent all known polymorphisms simultaneously, including, SNPs, indels, and various rearrangements, in a data-efficient manner. The edges can contain weights to reflect the likelihood of a path within the GGM incorporating any particular edge. The disclosure also provides for systems and methods for using the GGM as a reference model for the rapid assembly of short sequence reads and analysis of DNA sequence variation with enhanced computational efficiency.

33 Claims, 23 Drawing Sheets

Specification includes a Sequence Listing.

(51) Int. Cl.
*G06F 19/22* (2011.01)
*G06F 19/18* (2011.01)

(58) Field of Classification Search
USPC .................................................. 345/418, 440
See application file for complete search history.

(56) References Cited

U.S. PATENT DOCUMENTS

| | | | |
|---|---|---|---|
| 9,092,402 B2 | 7/2015 | Kural et al. | |
| 9,116,866 B2 | 8/2015 | Kural | |
| 2002/0150940 A1* | 10/2002 | Sykes | C12N 15/63 435/6.13 |
| 2009/0157368 A1* | 6/2009 | Van Marck | G06F 19/18 703/11 |
| 2012/0271827 A1* | 10/2012 | Merz | G06F 17/30985 707/737 |
| 2014/0349289 A1* | 11/2014 | Yeh | C12Q 1/6881 435/6.11 |
| 2015/0056613 A1* | 2/2015 | Kural | G06F 19/22 435/6.11 |
| 2015/0057946 A1 | 2/2015 | Kural | |
| 2015/0066381 A1 | 3/2015 | Kural | |
| 2015/0066383 A1 | 3/2015 | Wernicke | |
| 2015/0169823 A1* | 6/2015 | Chin | G06F 19/22 702/20 |
| 2015/0197815 A1 | 7/2015 | Kural | |
| 2015/0199472 A1 | 7/2015 | Kural | |
| 2015/0199473 A1 | 7/2015 | Kural | |
| 2015/0199474 A1 | 7/2015 | Kural | |
| 2015/0199475 A1 | 7/2015 | Kural | |
| 2015/0302145 A1 | 10/2015 | Kural et al. | |
| 2015/0310167 A1 | 10/2015 | Kural et al. | |
| 2015/0347678 A1 | 12/2015 | Kural | |
| 2016/0032390 A1* | 2/2016 | Hakonarson | G01N 33/5008 514/220 |

OTHER PUBLICATIONS

Phan, Vinhthuy, Shanshan Gao, Quang Tran, and Nam S. Vo. "How genome complexity can explain the hardness of aligning reads to genomes." In Computational Advances in Bio and Medical Sciences (ICCABS), 2014 IEEE 4th International Conference on, pp. 1-2. IEEE, 2014.*

Berger, B., et al., "Computational Solutions for Omics Data," Nature Reviews: Genetics 14(5):333-346, May 2013. (Author Manuscript provided, PMCID:PMC3966295, available in PMC Mar. 26, 2014, 30 pages).

Dilthey, A., et al., "Improved Genome Inference in the MHC Using a Population Reference Graph," Nature Genetics 47(6):682-688, Jun. 2015. (Author Manuscript provided, PMCID:PMC4449272, available in PMC Dec. 1, 2015, 25 pages).

Flicek, P., and E. Birney, "Sense From Sequence Reads: Methods for Alignment and Assembly," Nature Methods Supplement 6(11s):S6-S12, Nov. 2009. Corrigendum in: Nature Methods 7:479, Jun. 2010.

Kehr, B., et al., "Genome Alignment With Graph Data Structures: A Comparison," BMC Bioinformatics 15:99, Apr. 2014, 20 pages.

Paten, B., et al., "Cactus Graphs for Genome Comparisons," Journal of Computational Biology 18(3):469-481, Mar. 2011.

Paten, B., et al., "Mapping to a Reference Genome Structure," arXiv:1404.5010v1, Apr. 2014, 25 pages.

Ronagh, P., "Integer Optimization Toolbox: Minimizing Polynomials Over Integer Lattices Using Quantum Annealing," White Paper, 1QBit.com, Aug. 13, 2013, <http://demo.1qbit.com/>, 9 pages.

Simons Foundation, "University of California, Santa Cruz to Develop Human Genome Variation Map," Jan. 27, 2015, <https://simonsfoundation.org/features/foundation-news/university-of-california-santa-cruz-to-develop-human-genome-variation-map/> [retrieved Oct. 17, 2016], 2 pages.

Weisenfeld, N.I., et al., "Comprehensive Variation Discovery in Single Human Genomes," Nature Genetics 46(12):1350-1355, Dec. 2014. (Author Manuscript provided, PMCID:PMC4244235, available in PMC Jun. 1, 2015, 18 pages).

* cited by examiner (2 gap opens, 6 gaps, 0 mismatches)

Ref:    AAGCTA- -CTAG- - - -CT
Allele: AAGCTAGACTAGGAAGCT

FIG. 1A
*(PRIOR ART)*

(2 gap opens, 6 gaps, 0 mismatches)

Ref:    AAGCTA- - CT- - - - AGCT
Allele: AAGCTAGACTAGGAAGCT

FIG. 1B
*(PRIOR ART)*

(1 gap open, 6 gaps, 2 mismatches)

Ref:    AAGCTA - - - - - CTAGCT
Allele: AAGCTAGACTAGGAAGCT

FIG. 1C
*(PRIOR ART)*

(1 gap open, 6 gaps, 2 mismatches)

Ref:    AAGCTACT - - - - - AGCT
Allele: AAGCTAGACTAGGAAGCT

FIG. 1D
*(PRIOR ART)*

Alignment graph:

A-Bruijn graph:

Enredo graph:

Precursor cactus graph:          Cactus graph:

merge 3-edge connected components →

■ DARK BLUE
▦ LIGHT BLUE
▨ PURPLE
▩ PINK
▧ GREEN

■ DARK BLUE
▦ LIGHT BLUE
▨ PURPLE
▩ PINK
▧ GREEN

■ DARK BLUE
▦ LIGHT BLUE
▨ PURPLE
▩ PINK
▧ GREEN

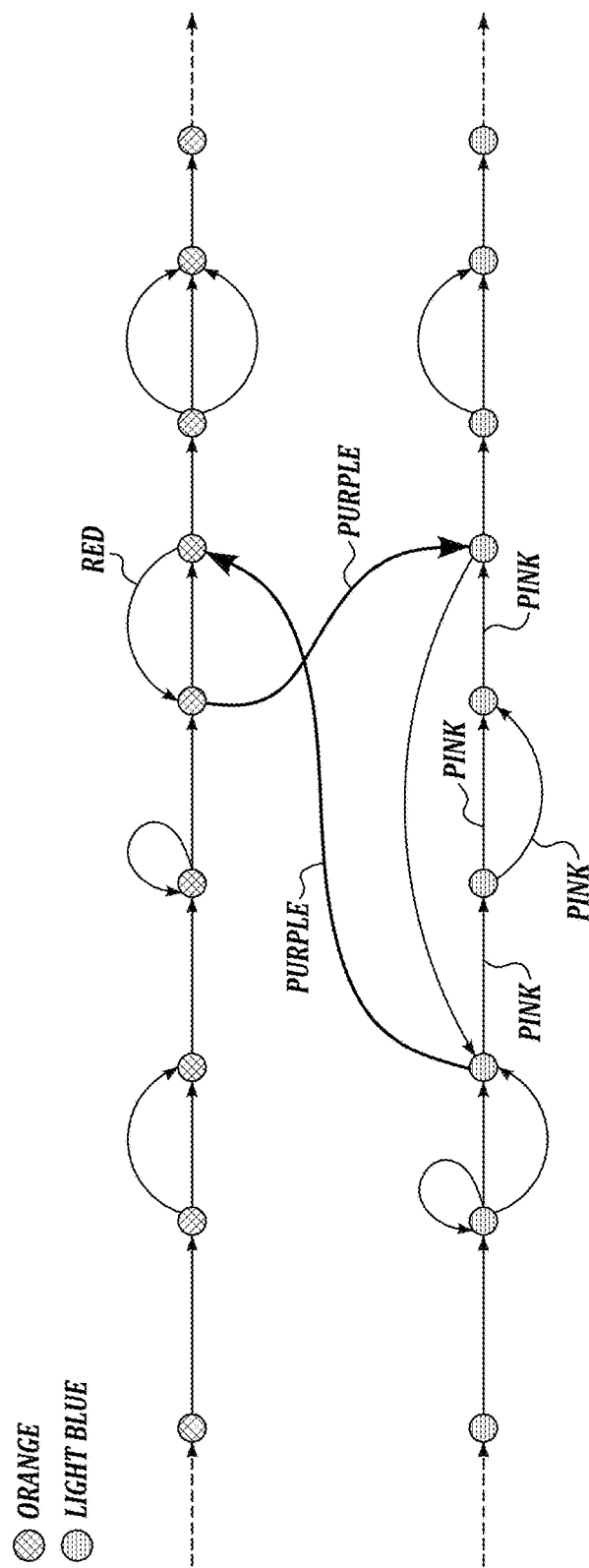

Chr21:
17000000-18000000
SNPs and short indels

METHODS FOR THE GRAPHICAL REPRESENTATION OF GENOMIC SEQUENCE DATA

CROSS-REFERENCE TO RELATED APPLICATION

This application claims the benefit of U.S. Provisional Patent Application No. 62/165,543, filed May 22, 2015, which is incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 56389_Seq_Final_2016-05-20.txt. The text file is 3.41 KB; was created on May 20, 2016; and is being submitted via EFS-Web with the filing of the specification.

FIELD OF THE INVENTION

This disclosure provides methods and systems for a computational framework to enhance the analysis of genomic information. More specifically, the disclosure provides graph-based reference genome, and methods and systems for generating and using the reference genome, that allow for the rapid assembly of sequence reads and determination of DNA sequence differences.

BACKGROUND

New advances in human DNA sequencing and computing technology are coming together to allow rapid identification of the complete genomes of individuals with striking potential for transforming personalized medicine. At present, key limitations to realizing the full potential of whole genome sequencing (WGS) include the time, expense, and reliability of processing DNA sequence data to generate the list of all variations present in an individual and to reveal those alterations that cause disease or modify the risk of disease. Advances in the analysis of genome sequences are, thus, critical for diagnosis and potentially informative for treatment. Accordingly, bioinformatics and innovation in computational methods are key drivers for improving the analysis and interpretation of DNA sequence data.

The current price of WGS is approaching $1,000 for the laboratory procedures, but the time and expense of computational analyses and genetic interpretation remains significantly higher. Currently, the most widely used approaches report the set of differences between an individual and a global reference genome sequence, as most of the 3 billion positions are the same. To obtain the set of differences, the most widely used computational approaches are based on a two-step process: (1) read mapping and (2) variant calling. The data produced in WGS is a collection of millions of short (e.g., ~150 letter) "reads", where each letter is one of the four canonical DNA nucleotides (A, C, G or T). These "reads" are then placed onto ("aligned against") a reference genome sequence in a manner akin to placing puzzle pieces onto a picture of the puzzle. Read mapping algorithms take a single read and scan through a reference genome to find where the read fits best. For each read there are billions of possible positions to be considered. Once all reads have been placed, there are usually redundant overlapping reads (on average 30-100 copies per position). An algorithm is then applied to pass over the 3 billion characters of the reference genome and evaluate statistically whether the mapped read data indicates a complete match to the reference genome at each position, or if there is evidence that the individual being sequenced differs from the reference either partially or completely.

However, the mapping of reads remains a significant challenge. Most of the single nucleotide variations from the reference genome present in any individual are polymorphic, meaning that many other individuals have the same sequence variation. It is estimated that roughly 85% of the variants found in each individual are polymorphic and 15% are rare variants. This variation can complicate alignment to the reference when sequence differences from the reference exist, potentially resulting in a failure to place the observed DNA sequence at the correct location. This reflects an allele bias in the reference. Reads that perfectly match the reference will be handled better than those that do not. Thus, the reference allele bias is a key source for errors in variant detection associated with the widely used practice of WGS analysis. The current approaches to this analysis is to select a reference sequence that is as similar to the new sequence as possible, and multiple approaches of this kind have been introduced (for example, using an ethnically similar reference genome for mapping). Such approaches are fundamentally oriented to using a reference which accounts for the common variants that are observed in a population. As a result, large-scale efforts are underway to provide a comprehensive inventory of human genetic variation, and to identify rare variants causal for genetic disorders and contributory to diverse diseases including for example, the dbSNP database, the HapMap project, and the 1000 Genomes project. In addition to these efforts, the recognition of the reference allele bias has also motivated efforts to develop alternative computational approaches to represent a reference genome that can efficiently include these known polymorphic locations and, therefore, allow improved read mapping. Such an approach would allow read mapping software to consider all recurring variations at each position, thereby eliminating or reducing the reference allele bias.

Another drawback to the existing alignment strategies is that the available reference genomes do not account for the existing variation that may be relevant for the comparison. For example, there is currently a global human reference genome (GRCh38) that is based on the combined genetic material of 13 anonymous individuals. A key limitation of the primary human reference genome is that it is but a single reference and does not account for known variations. For instance, if 51% of source people have an A at position X and 49% of source people have a C, the current reference genome would only report an A at that position. Beyond single character changes, the current reference genome also fails to allow for larger-scale properties, such as regions with variable numbers of repetitions or positions known to have variable structural rearrangements.

As indicated above, clinical WGS is dependent upon access to a reference genome, which provides the framework upon which sequence variation can be organized and reported. Much like solving a jigsaw puzzle, efficiency is significantly improved by the availability of a picture of the completed jigsaw to guide placement. As shown in FIGS. 1A-1D, the combined steps of alignment and variation calling are far from optimal as they fail to account for all available information and can product multiple, distinct results. Thus, any calling procedure introduces biases based on the reference one outgoing As an alternative to the current text-based reference genomes, graph-based models of DNA sequences have been explored. Graph models generally represent data using the concept of nodes and edges, where classically a node represents an observed property (e.g. a nucleotide at one position in a DNA sequence) and an edge represents movement from the previous position to the next. A variety of graph types having been introduced in the computer science field. Several common graph structures have been compared for their relevance to DNA sequence analysis (Kehr, B. et al. (2014) *BMC Bioinformatics* 15:99; incorporated herein by reference in its entirety). Common graph types such as De Bruijn graphs and string graphs have been used in procedures for de novo read assembly (see, e.g., Flicek, P. et al. (2009) *Nature* 6(11 Suppl):S6-S12; incorporated herein by reference in its entirety).

A graph-based reference genome has a number of advantages. It can represent all polymorphisms (recurrent variations) concurrently. Polymorphisms can be associated with a positional probability, allowing correlation between positions, as well as ethnic population differences (Dilthey, A. et al. (2015) *Nature Genetics* 47(6):682-8; incorporated herein by reference in its entirety), to be represented in a single graph. Importantly, graph models have a universally unique ID for each location (Paten B. et al. (2014) arXIV: 1404.5010; incorporated herein by reference in its entirety) as more insertions and deletions are discovered, allowing a reference to be updated as new data become available.

While a full reference genome based on graphs has not yet been created, efforts are underway to develop a human genome variation map as a mathematical graph based on a De Bruijn graph, which represents DNA sequence as nodes. De Bruijn graphs are a compressed data structure. However, in most cases an adjunct data structure, such as read pair information, is needed to map reads onto the graph.

Despite the advances in generating graph-based models of reference sequences, many challenges remain. For example:
  Linear representations allow for an unambiguous co-ordinate system and, thus, defining distances is simple. Within a flexible graph the represented components are relative and, therefore, searching for a particular region within the genome is a more complex problem.
  Current annotations use the fixed linear co-ordinates system, which may occur on multiple paths through the graph. Accordingly, a graph reference genome would need to link the annotations to all subgraphs that represent that section of the reference.
  The creation of randomized examples to serve as controls in an experiment is difficult.
  Updating the graph reference genome as new information is discovered can be difficult due to the relative and flexible nature of graph structures.
  File formats and incompatibility with current software and tools that are using the linear data structure create adoption problems.
  Graphs have only recently been used to perform read alignment on genomic data and, therefore, there are fewer algorithms developed that utilize graphs.
  Ease of visualization for large datasets. It can be difficult to view complicated non-planar data structures in a simple planar form.

Another significant challenge with the current graph model methods is the need for enormous storage requirements for computational analysis. Whereas DNA is diploid for humans (i.e., two copies of each chromosome with one from each parent), each reference genome is haploid. Additionally, graph models do not account for the diversity of DNA sequence variation observed within and between populations. It has been shown that using a population reference De Bruijn graphs that combine multiple reference sequences as well as SNPs and Indels improves the accuracy of alignment algorithms (Dilthey, A. et al. (2014) *Nature Genetics* 47(6):682-8). However, the human genomes used by popular algorithms such as BOWTIE are approximately 2.3GB in size without any "-omics" data. Hence, storing a complete picture of the human genome using current graph methods requires enormous storage and RAM. Thus, there remains a need for systems and methods to provide a reference genome that would capture all polymorphisms, such as single nucleotide changes, small insertions or deletions, and larger structural changes such as regional duplications, inversions, or translocations, as well as the correlations between all such variations, without creating an undue requirement for data storage and processing capacity.

A key challenge in genome analysis is the computational scale of the problems. Processing WGS can take multiple days on a multiple CPU supercomputer. In 2011, D-Wave Systems announced the first commercial quantum annealer, a new approach to supercomputing. Quantum computers optimize a function describing the system, over a set of candidate states using fluctuations (i.e., changes in the energy at points of the separable complex Hilbert space where the function operates). A quantum computer exploits superposition and entanglement, enabling it to consider all possible states simultaneously. To illustrate, there are over 6 billion base pairs in a human cell, and each location comprises of one of four nucleotides; hence, there are roughly 46 billion possible states. These numbers are simply too big for classical computers unless significant data compression techniques are used, which leads to loss or distortion of information. This new development in technology offers a chance to transform DNA analysis; to accelerate and improve the quality of clinical results by simultaneously evaluating all possible states for reference DNA. There is, however, a major challenge related to the technology. The most advanced processors can only handle 256 qbits, which limits the capacity of the system to work with only small graphs composed of a few hundred nodes. Accordingly, there is a need for a graph representation of the genome which sharply reduces the size. Likewise, there is a need for a graph representation that can be analyzed using parallel computing techniques that are currently available until quantum computers become more powerful.

Other approaches to develop a graph representation of the genome include the DISCOVAR algorithm, which uses a De Brujin graph in which observed DNA sequences are represented as edges (Weisenfeld, N. et al. (2014) *Nature Genetics* 46(12):1350-55; incorporated herein by reference in its entirety). However, the assembly graph created using DISCOVAR does not give a probabilistic weighting to the edges in accordance with other "-omics" data available. The assembly graph lacks the flexibility to select known variants and therefore create an updated reference genome based on known variations between populations, etc. The assembly graph is a unipath graph, which is a directed graph derived from the k-mer graph where each node represents a k-mer sequence. Furthermore, as a k-mer graph, the DISCOVAR procedure produces a compressed graph and requires adjunct data structure to perform read alignment (such as read pair information) and is, therefore, not be suitable for use in quantum computing.

Despite the advances of the art in generating reference genomic sequences for assembly of short reads, there remains a need to produce a reference graph that represents all relevant polymorphisms simultaneously in an efficient and compact manner to optimize data storage and processing capacity, such as through quantum computing. The present disclosure provides methods and systems that address these and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a computer-implemented method for updating a graph that represents a portion of a reference genome is provided. Each node of the graph includes a sequence position, and edges of the graph include sequences of characters from a genomic alphabet. A mutation record is obtained that includes one or more mutation sequences beginning at a mutation sequence start position and ending at a mutation sequence end position. A minimal spanning graph is identified within the graph that includes the sequence positions between the mutation sequence start position and the mutation sequence end position. A mutation start node is determined within the minimal spanning graph at the mutation sequence start position, and a mutation end node is determined within the minimal spanning graph at the mutation sequence end position. One or more paths are identified beginning at the mutation start node and ending at the mutation end node. Processing is performed for each path of the one or more paths, for each first node and second node within the path connected to each other by at least one edge, and for each mutation sequence of the one or more mutation sequences, wherein, in response to determining that no existing edge between the first node and the second node includes a portion of the mutation sequence between the sequence position of the first node and the sequence position of the second node, a new edge is created connecting the first node to the second node; and a portion of the mutation sequence is added between the sequence position of the first node and the sequence position of the second node to the new edge. Any contradictory edges or superfluous edges are removed from the graph after adding the new edges. The updated edges and nodes are stored in a graph data store.

In some embodiments, a computer-implemented method of aligning reads of a read sequence to a graph that represents a genome and polymorphisms therein is provided. The graph includes a plurality of edges. A set of bridges is selected from the graph. For each bridge in the set of bridges, a subset of a read pool is selected, wherein reads in the subset contain at least a portion of the bridge. For each read in the subset, a local alignment is performed for the read, the local alignment for the read is scored to generate a read-bridge pair score; and the read-bridge pair score is inserted into a score matrix. The score matrix is used to determine a best combination of placements of reads for the set of bridges, and the reads are placed on the graph.

In some embodiments, a system for generating graphs based on reference genome information is provided. The system comprises a graph data store and at least one computing device. The graph data store is configured to store a plurality of edge records, wherein each edge record includes a start node, an end node, a sequence listing, and a probability value. The at least one computing device is configured to obtain mutation records representing polymorphisms within the reference genome; and create and modify edge records within the graph data store based on the mutation records.

In some embodiments, a system for performing read alignments to a graph that represents a genome and polymorphisms therein is provided. The system comprises a graph data store, at least one bridge computing device, a plurality of alignment computing devices, and at least one matrix processing computing device. The graph data store is configured to store information representing the graph, the information including a plurality of edge records. The at least one bridge computing device is configured to receive a read pool; select a set of bridges from the edge records stored in the graph data store; for each bridge in the set of bridges: select a subset of the read pool, wherein reads in the subset contain at least a portion of the bridge; and transmit reads from the subset of the read pool and the bridge to an alignment computing device. The alignment computing devices are each configured to receive one or more reads and a bridge with which the reads are associated; perform a local alignment for each of the one or more reads; score the local alignment for each of the one or more reads to generate a read-bridge pair score for each of the one or more reads; and transmit the read-bridge pair scores to a matrix processing computing device. The at least one matrix processing computing device is configured to: receive read-bridge pair scores from the plurality of alignment computing devices; insert the read-bridge pair scores into a score matrix; use the score matrix to determine a best combination of placements of reads for the set of bridges; and place the reads on the graph.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 1A-1D are sequence alignments that illustrate mapping a DNA sequence read to a reference genome sequence. The image is derived from Paten B. et al. (2014) arXIV:1404.5010. Each sequence alignment in FIGS. 1A-1D have the same reference sequence (SEQ ID NO:1) and allele sequence (SEQ ID NO:2), but with different gaps and mismatches assigned to different positions. FIGS. 1A and 1B both have 0 mismatches and 2 gaps open (6 total gaps). FIGS. 1C and 1D both have a single gap open (6 total gaps) and 2 mismatches. There is no optimal method to select between the positions for the allele with respect to the reference genome without further information not contained within the text-based reference genome. The speed of alignment algorithms is a significant bottleneck to an analysis pipeline because the task of testing a read against all possible locations is computationally infeasible. Therefore, current algorithms often use a reference genome to find the most likely section where the best mapping will be located, favoring speed over accuracy. After a probable subset has been selected, slower algorithms with higher accuracy are used to optimize placement of the read.

FIG. 5A illustrates four individual assembled genomes with mutations (labelled as light blue, purple, pink, and green) highlighted against the dark blue linear reference genome. FIG. 5B illustrates how the four individual genomes may be merged to form a reference genome using existing multiple sequence alignment software. FIG. 5C illustrates a schematic representation of the GGM approach to generating a reference sequence with the sprouts algorithm. In this schematic, the dark blue line represents the linear human reference genome and additional data sets are added over depending on the order of linearity of the mutations. The coloured blocks stacked over the reference genome represent the mutations from the individuals shown in FIG. 5A.

FIG. 7A illustrates the original sequence ATGACCGACGAGATGAAA (SEQ ID NO:5) split between the nodes used later when the alternative alleles are included. FIG. 7B illustrates how a single nucleotide polymorphism, ATGACCGACGA[G/A]ATGAA (SEQ ID NO:6), would be represented in the GGM model. An edge (indicated as green) is inserted between nodes 6 and 7 with the alternative allele as the edge label. FIG. 7C illustrates how a deletion, ATGACCGAC[GAG/-]ATGAAA (SEQ ID NO:7), would be represented. An edge (indicated as blue) is inserted between nodes 5 and 7 of the reference sequence with an empty label. It is not necessary to connect the empty edge to node 6 as the deletion spans the SNP. FIG. 7D illustrates how an insertion, ATGACCGAC[CGACGAC-GA]GAGATGAAA (SEQ ID NO:8), would be represented. Repetitive elements are modelled as loop edges (indicated as yellow) in the graph. FIG. 7E illustrates how a translocation within a chromosome ATG[GAGATGAAA][ACCGA] (SEQ ID NO:9), would be represented. Tracing from left to right, the path containing the translocation travels along new edges edge from node 2 to node 5, labeled $1^{st}$ purple edge, continues along the reference graph until node 8, then travels back across the edge labeled 2nd purple to node 2 and then through nodes 3 and 4 before traversing the final edge, labeled $3^{rd}$ purple, connecting it to node 8 and completing the translocated sequence. FIG. 7F illustrates how a single nucleotide polymorphisms on an existing edge, ATGAC-CGACGAGAT[G/C]AAA (SEQ ID NO:10), would be represented in the GGM model. The existing edge is split by adding new nodes on either side of the mutation. An extra edge, labelled in red, is added to represent the alternative allele for that mutation. FIG. 7G illustrates the GGM model for all of the mentioned mutations in a single combined graph.

FIGS. 8A-8C schematically illustrate substructures in the GGM. FIG. 8A shows two illustrative GGM graphs representing different substructures, e.g., an "orange" chromosome and a "blue" chromosome. The edges shown in red on the orange chromosome and pink on the blue chromosome represent areas of the two chromosomes that are exchanged in an inter-chromosomal translocation. FIG. 8B illustrates the links between the two chromosomes at the break points of the translocation with the purple edges. FIG. 8C illustrates the two graph are rearranged to form linked subgraphs with purple edges showing the connections that represent the translocation between chromosomes.

FIG. 13A illustrates a FEK with the hashed arrow. FIG. 13B illustrates a highly probable FEK, which is determined during the later stages of the alignment algorithm when one of multiple possible edges is weighted heavily with a probability above a confidence threshold, and edges weighted with a probability below the confidence threshold are ignored when searching for FEKs.

FIG. 14A illustrates a manual recreation of the Cactus graph example (image obtained from "Cactus graphs for genome comparison," Paten et al., *J. Comput. Biol.* (2011) 18(3):469-81, incorporated by reference herein in its entirety) with the same blue and green paths shown. FIG. 14B illustrates a manually created GGM representation of the same sequence in FIG. 14A with the blue path highlighted. FIG. 14C illustrates a manually created GGM representation of the same sequence in FIG. 14A with the green path highlighted.

DETAILED DESCRIPTION

The present disclosure provides a graph-based reference genome framework referred to hereinafter as the GNOmics Graph Model (GGM) that can incorporate all known polymorphisms from standard data repositories, including SNPs, indels, and spatial and copy rearrangements, and related methods and systems for generating the GGM. The graph can be paired with a correlation table of the relationships between polymorphisms within a fixed distance, allowing for probabilistic determination of which positions are likely to show correlation in a sample.

As will be described in more detail below, the disclosed GGM method provides a graph model, and related methods and systems, for reference human genomes that use nodes for transitions and edges for sequence. Accordingly, reference genome constructed using the GGM method is defined by edges that are used to represent sequences that are essentially immutable. Variations that are highly likely can be represented as additional directional edges or nodes. A DNA sequence or subsequence of any length can be affixed to an edge. In some embodiments, edge can be assigned a probabilistic weighting (or likelihood) of the edge being present in genomic sample being assayed by WGS. The edge weighting can be inter-related with other edges depending on the path chosen through the graph. Additionally, the graph of the present disclosure permits a non-linear path such as a cycle to be traced, thus allowing for the analysis of sequences containing repetitive regions. In some embodiments, an interaction table is provided that specifies the correlation between edges within a population.

Figure 2:
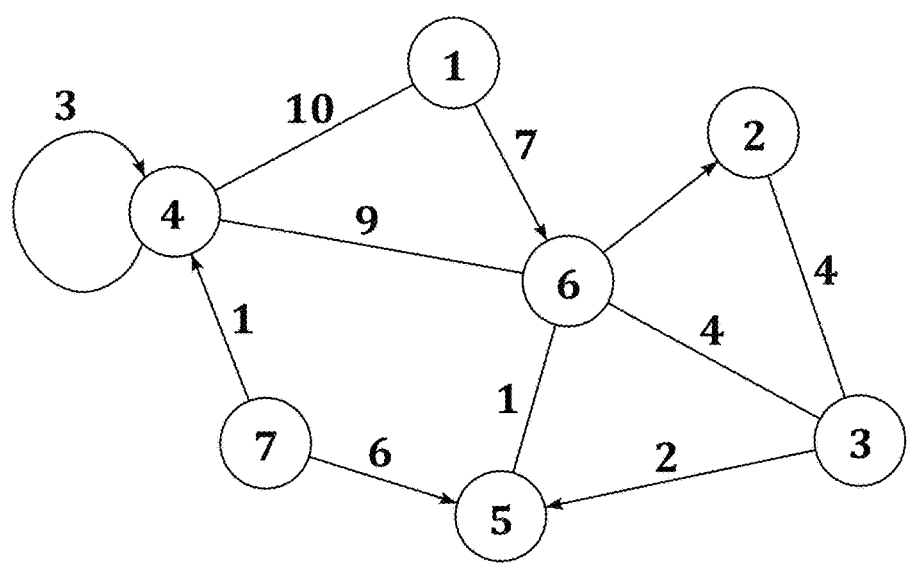
FIG. 2 illustrates a simple example of a mathematical graph structure. The graph has 7 nodes, and 10 edges. Each node is numbered, but not necessarily sequentially. Edges connect nodes with "lengths"/"weights" shown by the numbers above each edge. The 6 edges with arrows are directed edges (movement in one direction) and those without are undirected. The edge furthest to the left (with length 3) represents a loop where the start and end node are the same.
Figure 3A:
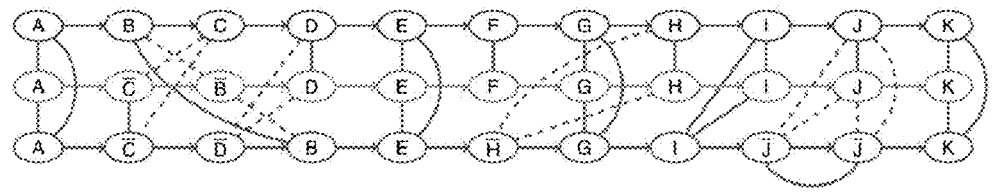
FIGS. 3A-3D illustrate four graph types depicting three distinct DNA sequences, with each sequence having eleven blocks. The image is derived from Kehr, B. et al. (2014) *BMC Bioinformatics* 15:99, incorporated herein by reference in its entirety. In each graph, the same three genomes consisting of 11 blocks of co-linear sequences are aligned to each other. In each of the graphs, it can be seen that there are 4 blocks with no large structural changes. In the alignment graph (FIG. 3A) there is a connection between the three genomes for each of the conserved blocks A, E, I and K. In the De-Bruijn (FIG. 3B) and enredo (FIG. 3C) graphs each of the three distinct paths pass linearly through these blocks, with the obvious extension that blocks A and K are source and sink nodes hence there are only edges exiting and entering, respectively. In the precursor cactus and cactus graph (FIG. 3D), the conserved edges represent singular connections between the larger subsections shown as the large grey circles, within which the structural changes are shown. The graphs also show structural rearrangements as the order of the blocks in two of the three paths (the green and red graphs) are not alphabetical. Deletions are shown by a missing block, such as block F for the red genome path and duplications are shown by repeating a block such as block J also in the red genome path.
Figure 3B:
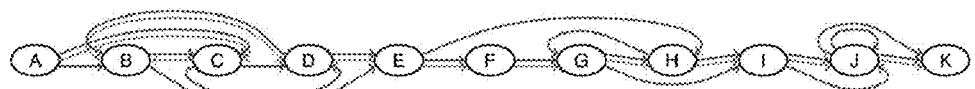
Figure 3C:
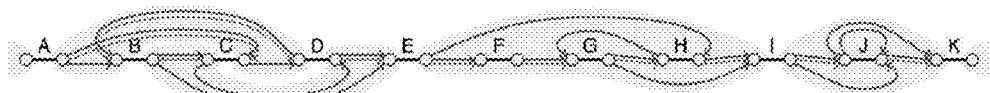
Figure 3D:
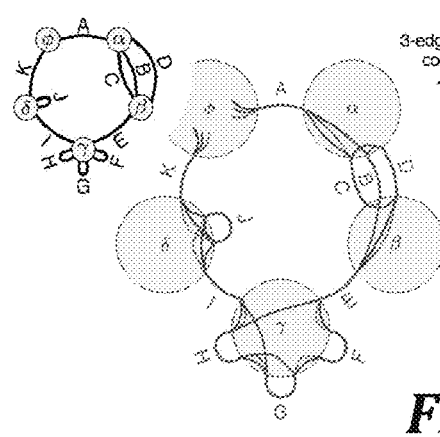
Figure 3D:
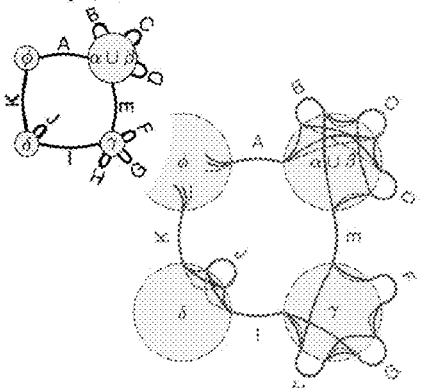

As used herein, the term "graph" refers to an ordered pair G=(V, E) comprising a set V of nodes and a set E of edges, which are 2-element subsets of V. An edge is connects two nodes. FIG. 2 shows a simple example of a mathematical graph. Heretofore, graph models have generally represented data using a node to represent an observed property (e.g., a nucleotide at one position in a DNA sequence) and an edge represents movement from the previous position to the next. Edges can be directed (indicating movement only in one direction) or undirected (indicating movement in both directions), and can be considered to have length. There are many types of graphs that have been developed in computer science and mathematics, ranging from simple to complex.

Figure 4:
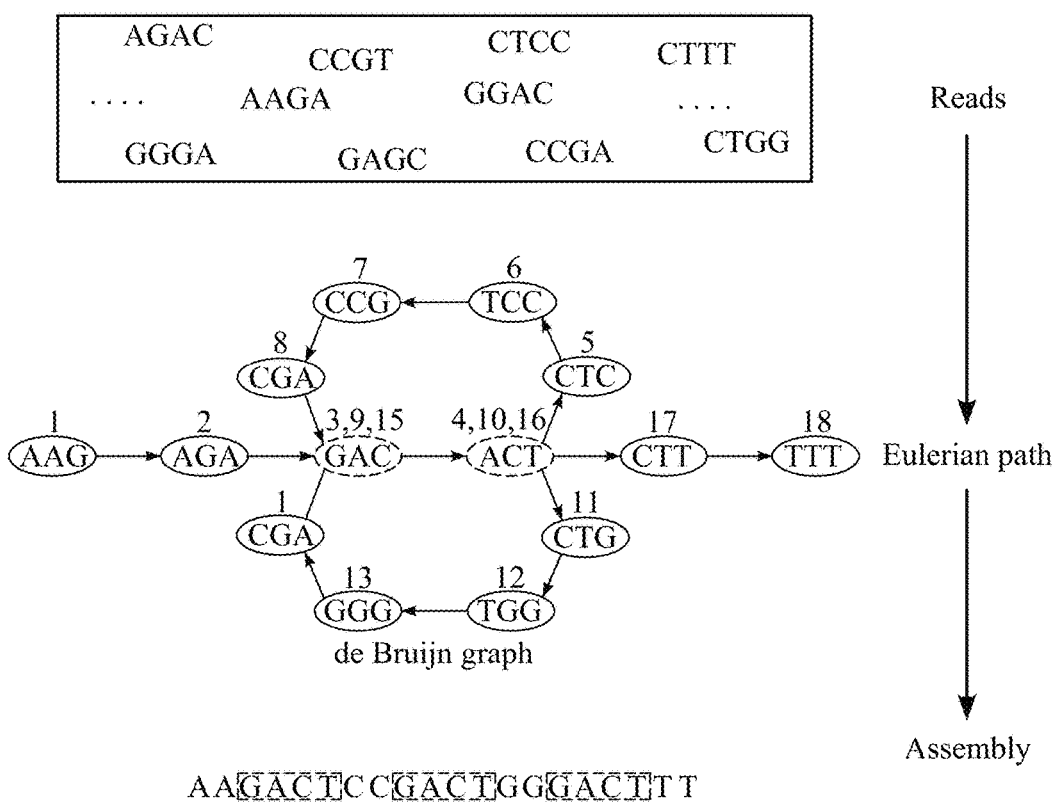
FIG. 4 schematically illustrates a De Bruijn graph of DNA sequence assembly, ultimately achieving the sequence set forth as SEQ ID NO:3 (see Berger, B., Peng, J., Singh, M. (2013) *Nature Reviews: Genetics* 14:333-346, incorporated by reference herein in its entirety).

The representation of DNA sequence using graph models has been previously explored. FIGS. 3A-3D provide several common graph structures (i.e., text alignment (3A), De Bruijn (B), Enredo (C), and cactus (D)) have been compared for their relevance to DNA sequence analysis, showing that transformations between the most common forms are trivial, indicating common underlying similarities. FIG. 4 shows an example of a De Bruijn graph, which have been used in procedures for de novo read assembly (i.e., genome sequence construction of short reads using a reference genome) as well as early stage reference construction.

As indicated above, a graph-based reference genome provides a number of anticipated advantages. It can represent all polymorphisms (i.e., recurrent variations) concurrently. Polymorphisms can be associated with a positional probability, allowing correlation between positions, as well as ethnic population differences, to be represented in a single graph. Importantly, graph models have a universally unique ID for each location as more insertions and deletions are discovered, allowing a reference to be updated as new data become available.

However, there are several challenges that currently exist in the construction of graph reference genomes. These drawbacks are described in more detail above, and include issues with logical coordinate designations, the ability to update the reference genome graph with new information, file and system compatibilities with current software and genomics tools that emphasize linear data structures, paucity of algorithms to align sequences to reference graphs, ease of visualization for non-planar data structures, difficulty of generating simulated and randomized examples for controls, and storage and computational limitations of current computer infrastructure in view of the enormous size of data involved.

The present disclosure provides for an efficient and compact approach for representing a reference genomic graph that addresses many of these challenges. The output of the disclosed graph approach is a computational framework for the representation of a reference genome sequence, the assembly of experimental short sequencing reads using the reference genome, and the analysis of genetic observed genetic variation. This technology is well suited for any organism in which multiple genome sequences are expected to be generated, including microbes, endangered species, species of agricultural importance, as well as humans and other vertebrates extensively used in research. The graph-based model of genetic variation created can be used for the detection and analysis of DNA sequence variation (ranging from single nucleotides polymorphisms to larger structural changes).

Embodiments of the present disclosure provide numerous technical advantages over previously attempted techniques. As one example, the graph model disclosed herein provides for a more compact representation of genomic information than existing techniques. Compared to a De Brujin graph wherein neighboring sequence information is repeated in adjacent nodes, the present graph model uses less storage space because no sequence information is repeated in neighboring edges. As another example, because the graph model disclosed herein uses a cyclic graph, repeated sequences can be compressed into a single repeating edge instead of requiring each repetition to be listed, thereby further reducing the required storage space. As a further example, the techniques disclosed herein for performing a read alignment using the graph model reduce the time needed for the read alignment because they provide the ability to use parallel computing resources to concurrently process multiple reads from read pools. As still another example, the graph model disclosed herein provides enhanced visualization and analysis characteristics compared to previous techniques. A key concept underlying the invention is the generation of a graph model for a reference genome sequence uses nodes for transitions and edges for sequence. This is the reverse of classic approaches described above. A full reference genome can be constructed using a graph in which edges represent sequences that are essentially lack variation, and are thus collapsed into a single edge representation. Polymorphisms that are likely to occur, such as single or multiple nucleotide polymorphisms, insertions, deletions, rearrangements (e.g., translocations) can be represented as additional directional edges or nodes. See, e.g., FIGS. 7A-7G.

In some embodiments of the disclosed model, each of the edges carries a weight that is inter-related with other edges, depending on the path chosen through the graph. This reflects the fact that certain portions of the genome are linked, and tend to stay together over time. This phenomenon results in haplotype blocks that can be observed in the population. Thus, the detection of a particular edge influences the assignment of a weight to a linked edge at a distinct location in the graph.

As represented, each node is simply a placeholder within the graph but does not directly correlate to a particular base pair location. However, in an illustrative implementation, the nodes can have a position label from the current reference genome GRCH38 to ease transitions and population of the graph. The nodes do not have any associated weighting. A path through the graph represents a potential haploid reference genome.

The disclosure provides a novel graph model representation that overcomes limitations of established models, providing many benefits by combining an edge labeled cyclic graph with a probabilistic cost function based on known genetic information. Generally described, the following characteristics are combined within the GGM realize the benefits over existing graph models described above. First, DNA sequence information is recorded as labels on the edges, rather than the common use of DNA sequence labels being affixed to nodes. DNA sequence of any length of letters can be affixed to an edge and typically represent stretches of reference sequence that have no, or likely to have low, variation in the reference population and, thus, can be collapsed into a single edge representation to conserve computational and representational resources. Edges can be assigned "costs" or weights, which relate to the probability of the edge being present in a sample, e.g., the probability of the target genome being sequenced will have the indicated sequence. This weight can be initially applied based on, for example, known prevalence in a relevant reference population or subpopulation. The weights can be adjusted in light of observed properties during an analysis. The model allows for non-linear paths to be traced and, thus permit illustration of cycles representing repeating segments. Finally, the model can include an interaction table (i.e., a meta-graph), which specifies the correlation between (i.e., the linkage or the co-occurrence of) edges within a population.

By shifting sequence to the edges of the graph and allowing any length of letters to be combined, long invariant segments of the genome can be compressed. The GGM is flexible and allows for simple addition of variants, by breaking an edge into two pieces by the insertion of additional nodes and/or edges. The flexibility of the model allows for representation of cycles to indicate repeated structures and structural rearrangements/inversions in a compact manner compared to the established graph models.

Figure 19:
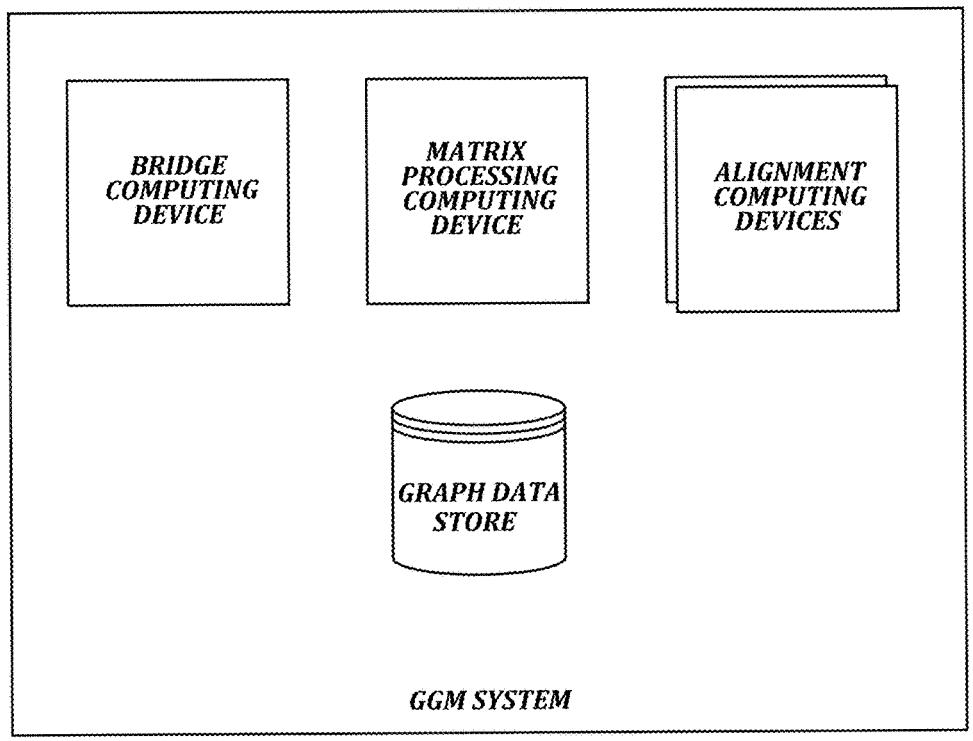
FIG. 19 is a block diagram that illustrates an exemplary embodiment of a system for performing read alignments according to various aspects of the present disclosure.

FIG. 19 is a block diagram that illustrates an exemplary embodiment of a system for performing read alignments according to various aspects of the present disclosure. As illustrated, the GGM system includes a bridge computing device, a matrix processing computing device, a plurality of alignment computing devices, and a graph data store. The graph data store is configured to store one or more GGM graphs as discussed herein. The bridge computing device is configured to receive a read pool. The read pool may be generated by a sequencing device, or may be obtained from a data store. The bridge computing device selects a set of bridges (or FEKs) from a GGM graph stored in the graph data store. For each bridge, the bridge computing device selects a subset of the read pool wherein the reads contain at least a portion of the bridge, and transmits the subset of the read pool and the bridge to the plurality of alignment computing devices for alignment. The alignment computing devices perform local alignments for the reads and scores the local alignments to generate read-bridge pair scores. The local alignment may be performed using any suitable technique, including but not limited to using a Smith-waterman algorithm, dynamic programming, or position-specific scoring matrices. The alignment computing devices then transmit the read-bridge pair scores to the matrix processing computing device, which adds the scores to a score matrix, and uses the score matrix to determine a best combination of placements of reads for the set of bridges. The best combination may be determined using any suitable technique, including but not limited to performing an eigenvalue decomposition, a spectral mapping, or a functional analysis using Hilbert or Banach spaces. The reads are then placed on the graph, and the alignment may be stored in the graph data store.

In some embodiments, some of the illustrated computing devices, such as the bridge computing device, the matrix processing computing device, and/or a computing device that provides the graph data store, may be combined into a single computing device. In some embodiments, the functionality of one or more of the illustrated computing devices may be separated into multiple computing devices. In some embodiments, the illustrated computing devices may be communicatively coupled to each other over any type of suitable network or other communication technology.

Figure 20:
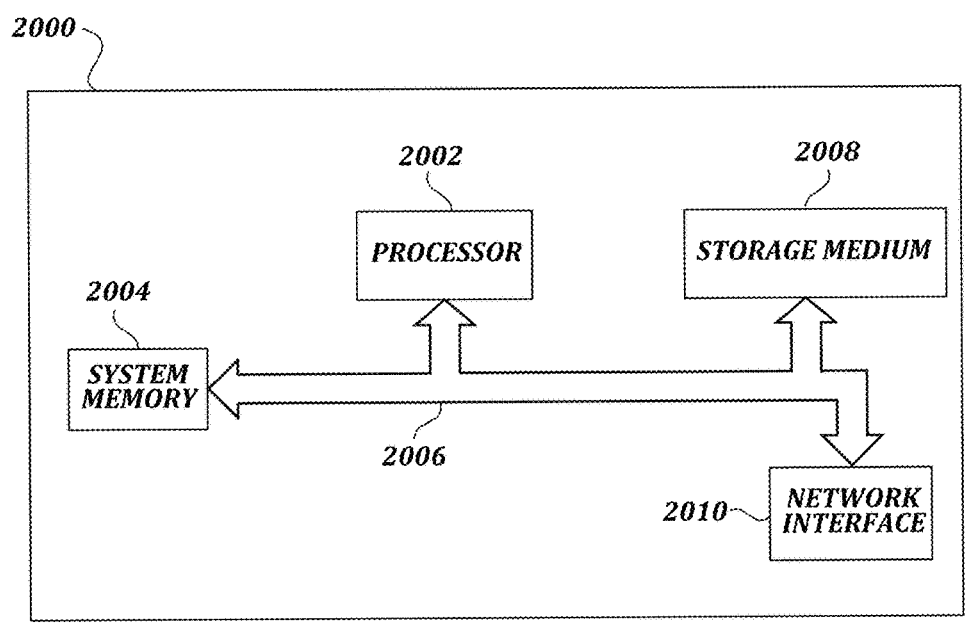
FIG. 20 is a block diagram that illustrates various aspects of an exemplary computing device suitable for use with embodiments of the present disclosure.

FIG. 20 is a block diagram that illustrates aspects of an exemplary computing device 2000 appropriate for use with embodiments of the present disclosure. While FIG. 20 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 2000 may be any one of any number of currently available or yet to be developed devices.

In its most basic configuration, the computing device 2000 includes at least one processor 2002 and a system memory 2004 connected by a communication bus 2006. Depending on the exact configuration and type of device, the system memory 2004 may be volatile or nonvolatile memory, such as read only memory ("ROM"), random access memory ("RAM"), EEPROM, flash memory, or similar memory technology. Those of ordinary skill in the art and others will recognize that system memory 2004 typically stores data and/or program modules that are immediately accessible to and/or currently being operated on by the processor 2002. In this regard, the processor 2002 may serve as a computational center of the computing device 2000 by supporting the execution of instructions.

As further illustrated in FIG. 20, the computing device 2000 may include a network interface 2010 comprising one or more components for communicating with other devices over a network. Embodiments of the present disclosure may access basic services that utilize the network interface 2010 to perform communications using common network protocols. The network interface 2010 may also include a wireless network interface configured to communicate via one or more wireless communication protocols, such as WiFi, 2G, 3G, LTE, WiMAX, Bluetooth, and/or the like.

In the exemplary embodiment depicted in FIG. 20, the computing device 2000 also includes a storage medium 2008. However, services may be accessed using a computing device that does not include means for persisting data to a local storage medium. Therefore, the storage medium 2008 depicted in FIG. 20 is represented with a dashed line to indicate that the storage medium 2008 is optional. In any event, the storage medium 2008 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

As used herein, the term "computer-readable medium" includes volatile and non-volatile and removable and non-removable media implemented in any method or technology capable of storing information, such as computer-readable instructions, data structures, program modules, or other data. In this regard, the system memory 2004 and storage medium 2008 depicted in FIG. 20 are merely examples of computer-readable media.

Suitable implementations of computing devices that include a processor 2002, system memory 2004, communication bus 2006, storage medium 2008, and network interface 2010 are known and commercially available. For ease of illustration and because it is not important for an understanding of the claimed subject matter, FIG. 20 does not show some of the typical components of many computing devices. In this regard, the computing device 2000 may include input devices, such as a keyboard, keypad, mouse, microphone, touch input device, touch screen, tablet, and/or the like. Such input devices may be coupled to the computing device 2000 by wired or wireless connections including RF, infrared, serial, parallel, Bluetooth, USB, or other suitable connections protocols using wireless or physical connections. Similarly, the computing device 2000 may also include output devices such as a display, speakers, printer, etc. Since these devices are well known in the art, they are not illustrated or described further herein. Unless specifically defined herein, all terms used herein have the same meaning as they would to one skilled in the art of the present invention.

As understood by one of ordinary skill in the art, a "data store" as described herein may be any suitable device configured to store data for access by a computing device. One example of a data store suitable for use with the high capacity needs of the systems disclosed herein is a highly reliable, high-speed relational database management system (RDBMS) executing on one or more computing devices and accessible over a high-speed network. However, any other suitable storage technique and/or device capable of quickly and reliably providing the stored data in response to queries may be used, such as a key-value store, an object database, and/or the like. Further, the computing device or devices providing the data store may be accessible locally instead of over a network, or may be provided as a cloud-based service. A data store may also include data stored in an organized manner on a computer-readable storage medium. One example of a data store which includes reliable storage but also low overhead is a file system or database management system that stores data in files (or records) on a computer-readable medium such as flash memory, random access memory (RAM), hard disk drives, and/or the like. One of ordinary skill in the art will recognize that separate data stores described herein may be combined into a single data store, and/or a single data store described herein may be separated into multiple data stores, without departing from the scope of the present disclosure.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denote one or more, unless specifically noted.

Unless the context clearly requires otherwise, throughout the description and the claims, the words "comprise," "comprising," and the like are to be construed in an inclusive sense as opposed to an exclusive or exhaustive sense; that is, to indicate in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

Publications cited herein and the material for which they are cited are hereby specifically incorporated by reference in their entireties.

The following examples are provided for the purpose of illustrating, not limiting, the material disclosed herein.

EXAMPLES

Example 1

This example describes the storage of DNA sequences as edge labels on a directed connected graph, which can represent a reference genome containing common variants observed for a species or a sub-population of a species.

Figure 6A:
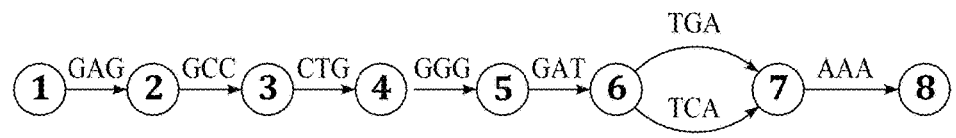
FIG. 6A is a representation of the sequence GAGC-CTGGGAT[G/C]AAA (SEQ ID NO:4) using overlapping 3-mers as in a De Bruijn graph.
Figure 6B:
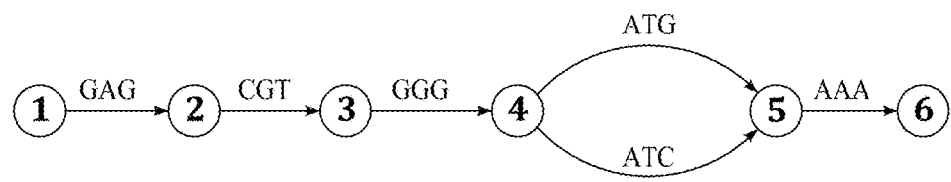
FIG. 6B is a representation of the same SEQ ID NO:4 using non overlapping 3-mers as in a De Bruijn graph.
Figure 6C:
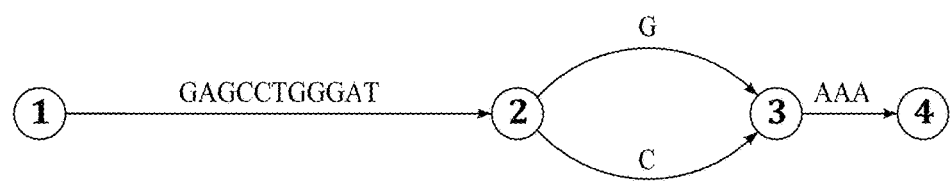
FIG. 6C is a representation of the same SEQ ID NO:4 using the GNOmics Graph Model (GGM) model showing how long conserved sequences can be placed in the graph as a single edge which makes the graph more compact and hence more computationally-efficient.
Figure 7A:
FIGS. 7A-7G illustrates examples of simple sequence polymorphisms as depicted using the GGM model of the present invention.
Figure 7B:
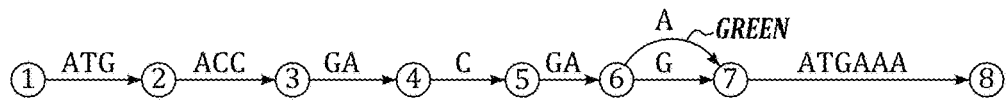
Figure 7C:
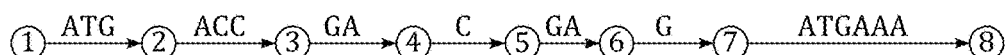
Figure 7D:
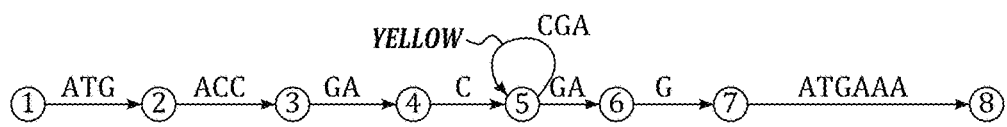
Figure 7E:
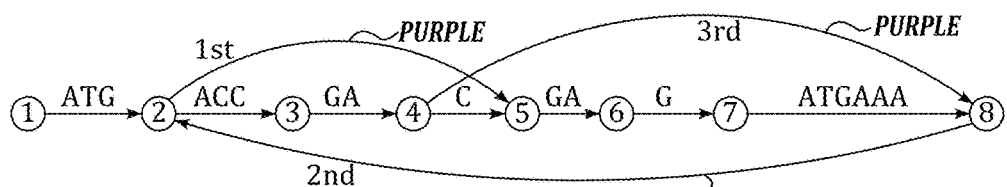
Figure 7F:
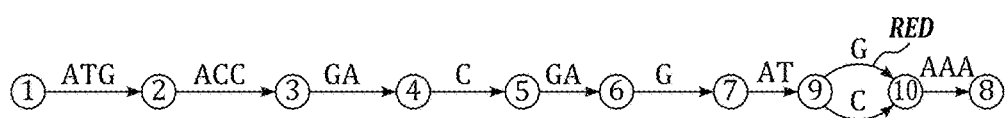
Figure 7G:
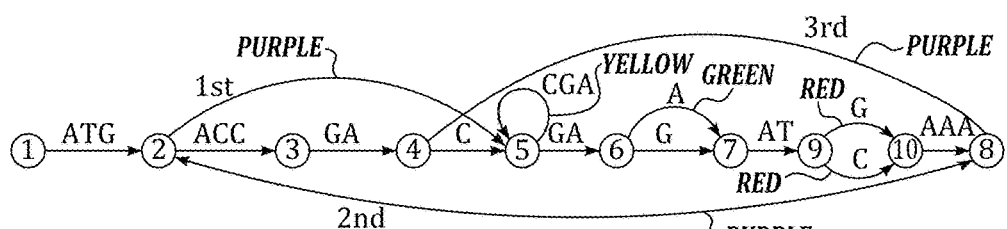

Unlike De Bruijn graphs, the GNOmics Graph Model (GGM) approach of the current invention does not display overlap in the sequence label between adjacent edges. This is because each polymorphism is represented by a unique edge within the subgraph correlating to that sequence. In FIG. 6A the sequence requires 8 nodes and 8 edges using a De Bruijn graph structure with 3-mers that overlap by 1. Removing the overlap of the illustrated k-mers reduces the number of nodes and edges to six each. See FIG. 6B. A further reduction can be gained by using the GGM model, as shown in FIG. 6C, which only requires 4 nodes and 4 edges. The result of implementing the GGM is a mutable graph reference genome that incorporates all known polymorphisms from standard data repositories, including SNPs, indels, and spatial and copy rearrangements paired with a correlation table of the relationships between polymorphisms within a fixed distance. By selecting characteristics such as population (Dilthey, A. et al. (2015) *Nature Genetics* 47(6):682-688; incorporated herein by reference in its entirety), a personalized graph reference genome is created for more accurate read alignment.

The present GGM approach (also referred to herein as "GRAPH") results in the directed connected graph M consisting of the directed edges E and the vertices V, i.e., M=(V, E).

For the representation of genome sequence variation, the GGM approach provides a method to store genomic sequence as edge labels on a directed connected graph, which represents a reference genome with common variations for a species or population. The capacity to represent all variation types within the same framework is an important advance compared to existing graph models. The approach allows for long stretches of non-variable sequence to be compacted into a single edge, thereby reducing the number of nodes and edges dramatically and as a consequence reduces the computational requirements needed for sequence analysis.

Each edge has an associated transition probability or edge weight, and a label which represents a DNA sequence of any number of nucleotides. The length of an edge is defined as the number of nucleotides on the label. An edge label may be empty, which represents a transition without any associated sequence length. An edge has a primary direction which matches with reading the label from left to right (e.g., 5' to 3' for a DNA sequence). If an edge is traversed in reverse of its primary direction then the label sequence is replaced by its reverse complement sequence (e.g., 5'-CAGT-3' becomes 5'-ACTG-3'). Each vertex may be labelled with the associated base pair coordinate from one or more text-based reference genomes for the species being studied, e.g., GRCH37 and GRCH38 for humans, corresponding to the coordinate of the next edge label nucleotide represented in the text-based genome. This enables cross compatibility with text-based reference genomes.

Example 2

This example describes how the use of the GGM allows the representation of sequence variations.

Figure 8A:
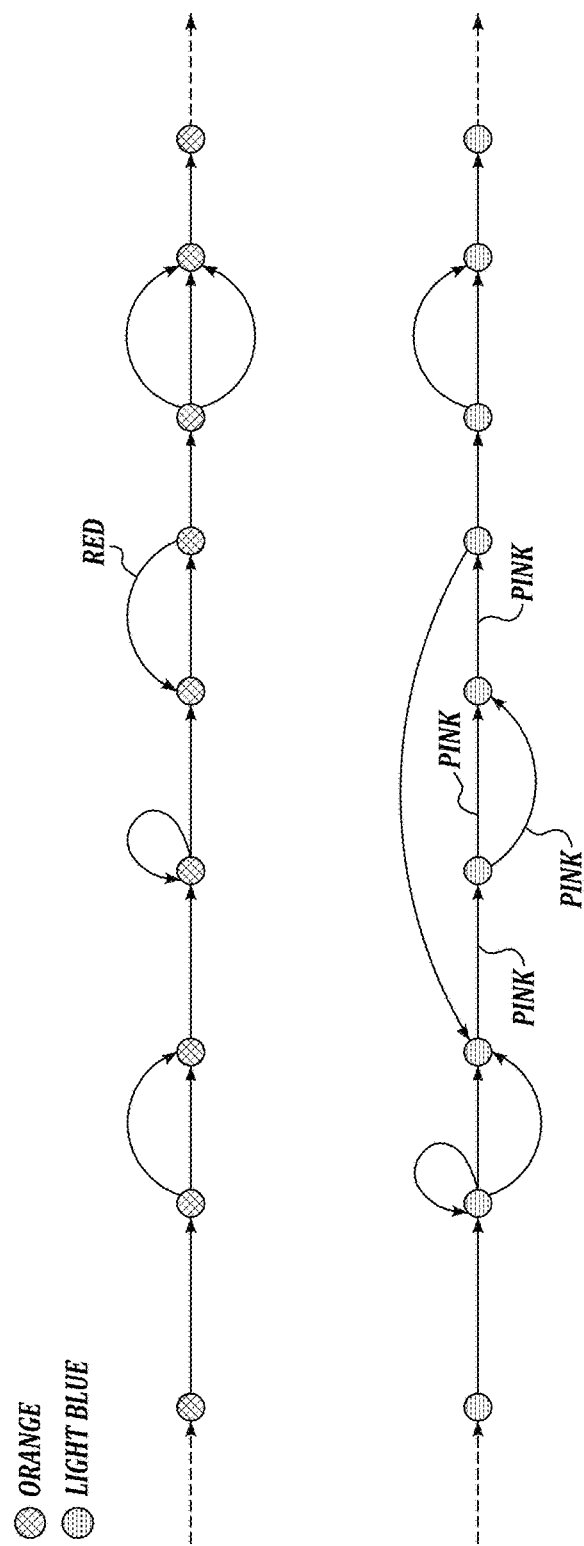
Figure 8C:
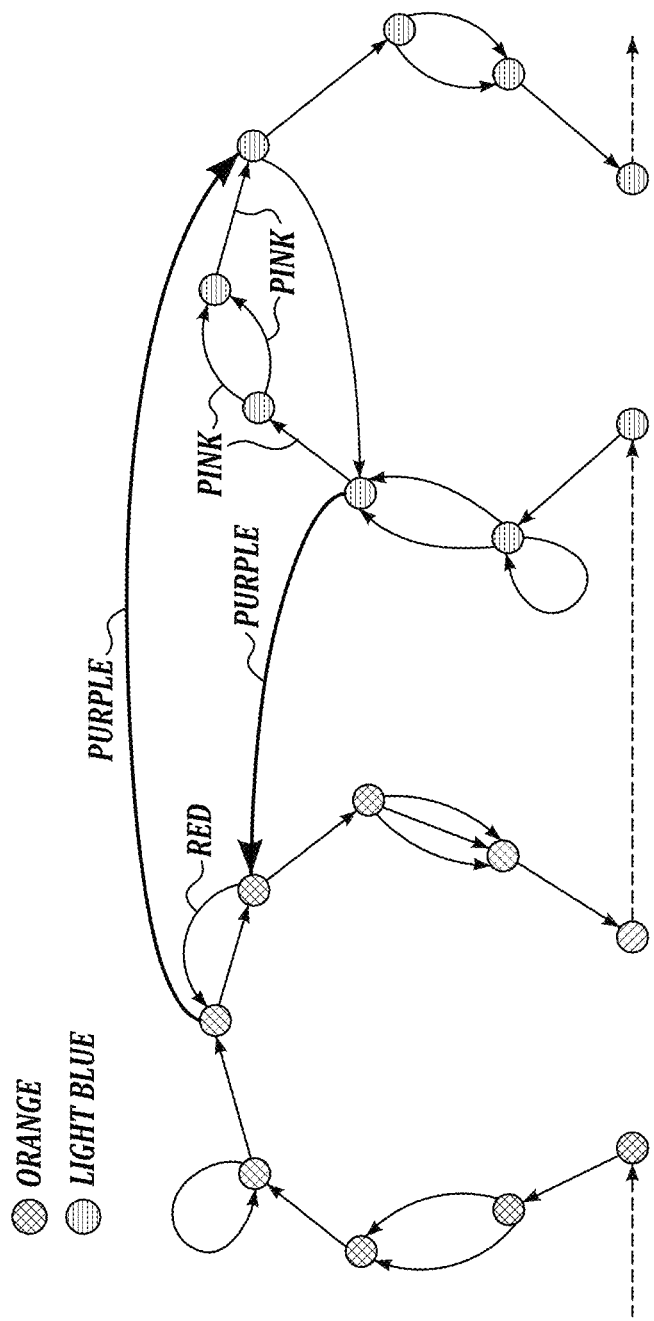
Figure 9:
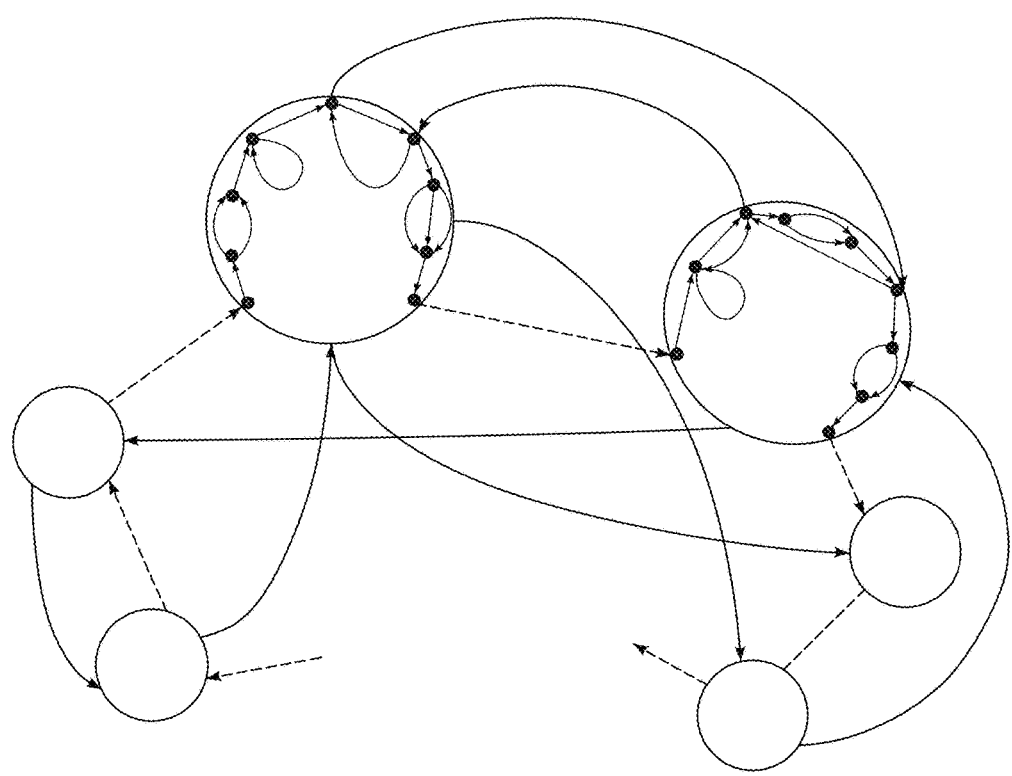
FIG. 9 illustrates a representation of a whole genome graph where each of the chromosomes can be a subgraph. This is an alternative to FIGS. 8A-8C where the chromosomes were represented as linear subgraphs. Each of the larger circles in FIG. 9 represents a more complex subgraph with the dotted lines showing the sequential ordering and the solid lines showing inter-subgraph mutations and rearrangements.

The GGM approach allows for the simple introduction of sequence variants, by breaking an edge into two pieces. Other sources of sequence variation such as structural rearrangement, repeated sequence elements and inversions can be accommodated by using cycles. FIGS. 7A-7G illustrate the methods used to represent different mutations using the GGM approach including but not limited to single character mutations, insertions, deletions, inversions, intra-translocation, inter-translocation and copy number variations. Substructures of existing reference genomes, such as chromosomes, can be represented as subgraphs (see FIGS. 8A and 8B), wherein the subgraphs are connected linearly to establish an order of the substructures as shown in FIG. 8C (e.g., by chromosome number). However, the subgraphs may also be connected across substructures if such genetic variations are observed that span multiple substructures, as shown in FIG. 9.

Example 3

This example describes the comparison between the cactus graph model and the GGM.

Figure 14A:
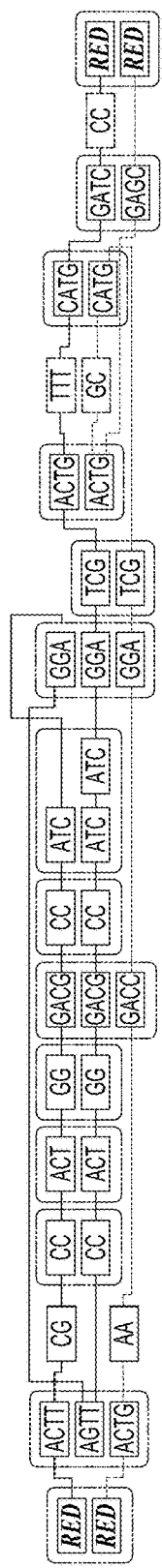
FIGS. 14A-14C illustrate a comparison of a GGM to a Cactus graph.
Figure 14B:
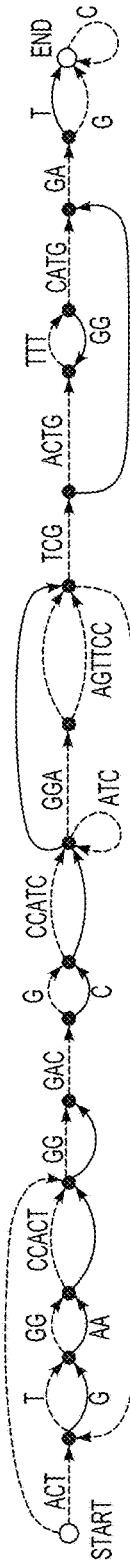
Figure 14C:
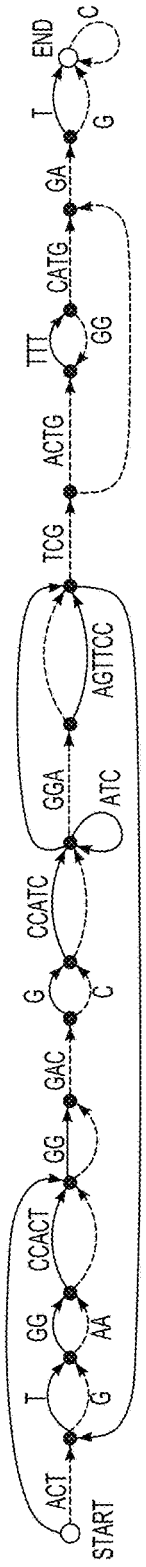

For comparison of the GGM to an existing graph model, the same sequence region is displayed using a cactus graph (FIG. 14A) and the GGM (FIGS. 14B and 14C). The illustration delineates two alleles for the same region (a "green" allele and a "blue" allele), where one allele is anticipated to be derived from each parent. The cactus graph includes 37 nodes and 36 edges, whereas the GGM uses 17 nodes and 31 edges to represent the same number of characters. Most approaches to genome alignment and construction using graph structures use the idea of tracing a path through the graph to generate the linear representation of the genomic sequence. Dijkstra's algorithm is one of the most well-known algorithms for finding the shortest paths between nodes in a graph and it has a running time of $O(|V|2)$ with some improvements made for special cases of graphs. Therefore, any reduction in the number of nodes in a graph will dramatically reduce the running time for shorted path algorithms. It is evident that an overall reduction in both nodes and edges will reduce the storage requirements for a graph.

Example 4

This example describes an illustrative algorithm for the creation of a GGM.

Figure 5A:
FIGS. 5A-5C are schematic representations of multiple sequence alignment algorithms used for reference construction.
Figure 5B:
Figure 5C:
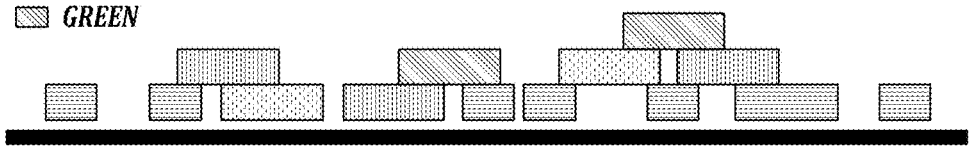

An illustrative algorithm used for the GGM approach is called Sprouts and is based on the classical computer science problem known as "Game of Sprouts." The concept is that the GGM is sprouting and, hence, is built from a bottom-up approach. In traditional multiple sequence alignment (MSA) algorithms used for reference construction, the complete sequences of multiple individuals are merged at places where there is no variation, thus creating a single reference sequence that is most representative. This process is depicted pictorially in FIGS. 5A and 5B. In contrast, with the sprouts algorithm, the smallest data set is used and additional data sets are added on top in accordance with the order of linearity of the mutations, as shown pictorially in FIG. 5C. Each time a new mutation is added to the model it creates a new possible path in the reference GGM model. In this manner, this allows the mutations included in the reference GGM to be constrained by type, size or other attributes.

Figure 10:
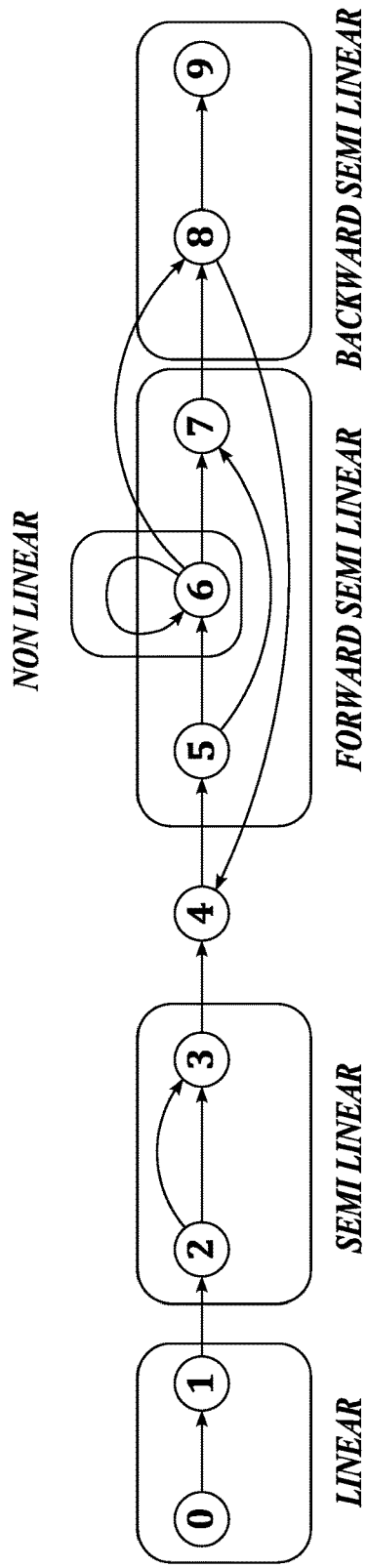
FIG. 10 is a schematic representation of the linearity of various types of mutations.

In order to automate the process, the linearities of mutations are defined within the GGM approach as shown in FIG. 10. Linear mutations are defined as single forward edges between adjacent nodes in ascending order. Examples of linear mutations include bridges in the graph with conserved sequences and no known mutations. Semi-linear mutations, which include mutations with no overlap to other mutations such as SNPs and INDELS, are defined as multiple forward edges between adjacent nodes in ascending order. Forward semi-linear mutations are defined as the start of a region with multiple overlapping mutations. These are depicted within the GGM as multiple forward edges between a single node and higher nodes. Backward semi-linear mutations correspond to the end of a region with multiple overlapping mutations and are represented as multiple forward edges from multiple lower nodes to a single node. Non-linear mutations are defined as multiple unordered incoming and outgoing edges, which can include loops representing sequence repeats or insertions, as well as highly mutated regions.

The reference string is generated by, for example, concatenating the multiple lines of a fasta file or using known existing reference co-ordinates. This reference string is set as a simple graph, with two nodes and a labeled edge representing the entire string. If the string is too large to be loaded on the computer, then the algorithm can be converted to work under a divide and conquer method, creating subgraphs for smaller regions and then merging the graphs afterwards.

If the mutations are provided as a list of known mutations from standard public databases, then a file (e.g., a vcf file) is created from the GNOmics database. Otherwise an input file (e.g., a vcf file) given is formatted to select the following information:

Chr, start_bp, stop_bp, strand, var_key, prefix, id, type, ref_allele, alt_1_allele, alt_2_allele, alt_3_allele The file is read by individual lines, allowing for further parallelisation. The file can be converted so that each mutation is defined for the positive strand of the reference sequence should there be multiple strands.

For each type of mutation, the nearest start and end nodes are identified in the graph, and if necessary new nodes are created to represent the mutations start and end point and the original reference sequence is split around the new nodes. New edges are added to represent the alternative alleles for each mutation with rsnum, weight, mutation type, and colour as attributes. The rsnum allows the mutation to be linked to current databases. The colour is based on the mutation type which is inputted from the vcf file.

To update the GGM as new genetic information is received, the linearity of the mutation is determined. If coordinate information is known, for example, if the GRCH37/38 coordinates are known, then the mutation can be parsed through the Sprouts algorithm. If coordinates are not known, then flanking sequence information can be used to select subgraph containing the region.

Example 5

This example describes the construction of an illustrative GGM for chromosome 21.

Figure 11:
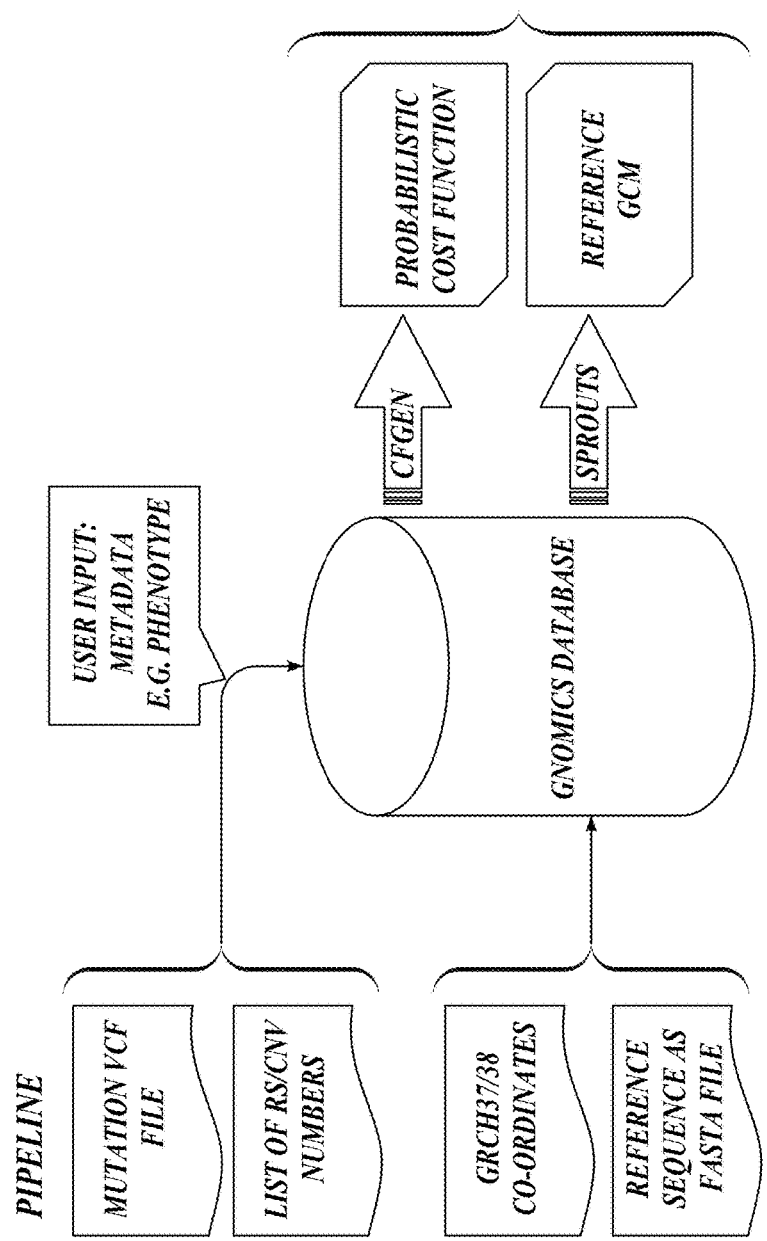
FIG. 11 is a schematic of the pipeline for the GGM method. The two algorithms that generate the cost function and the reference GGM are CFgen and Sprouts, respectively.
Figure 12:
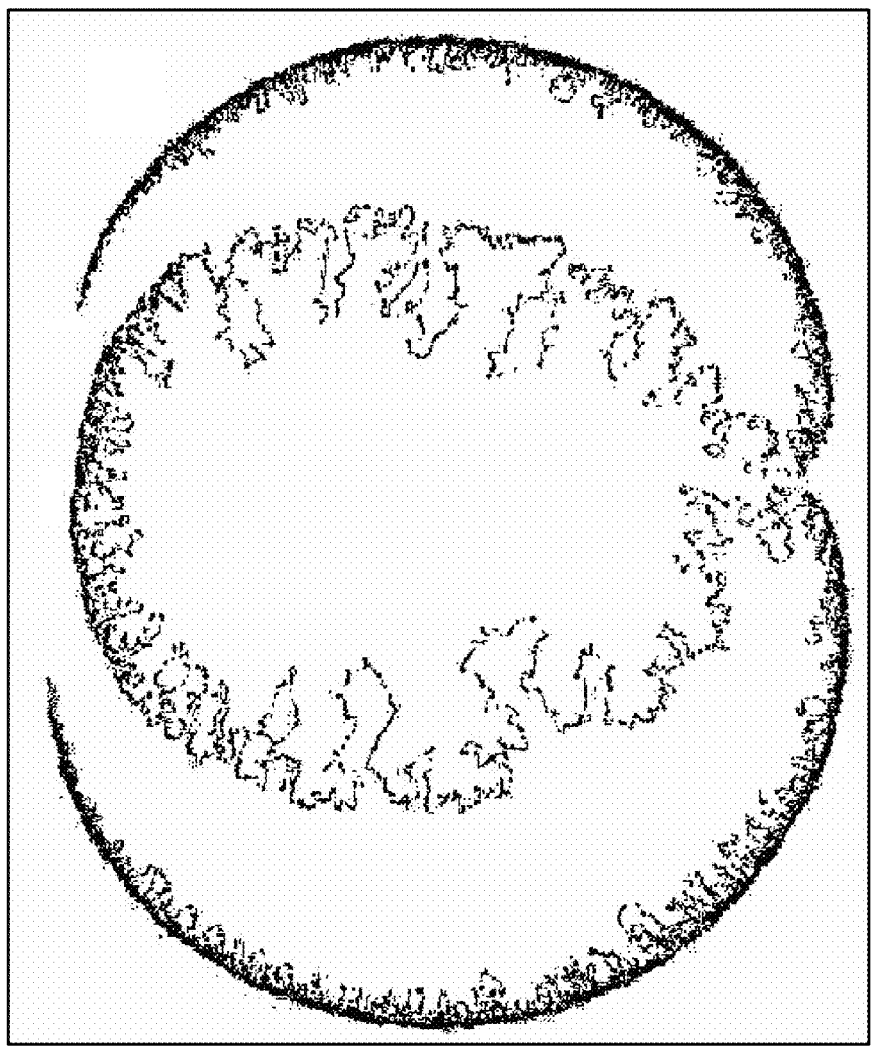
FIG. 12 illustrates a subsection of chromosome 21 (17,000,000 to 18,000,000) using the GGM model to indicate basic mutations (e.g., SNPs and short INDEL S).
Figure 18:
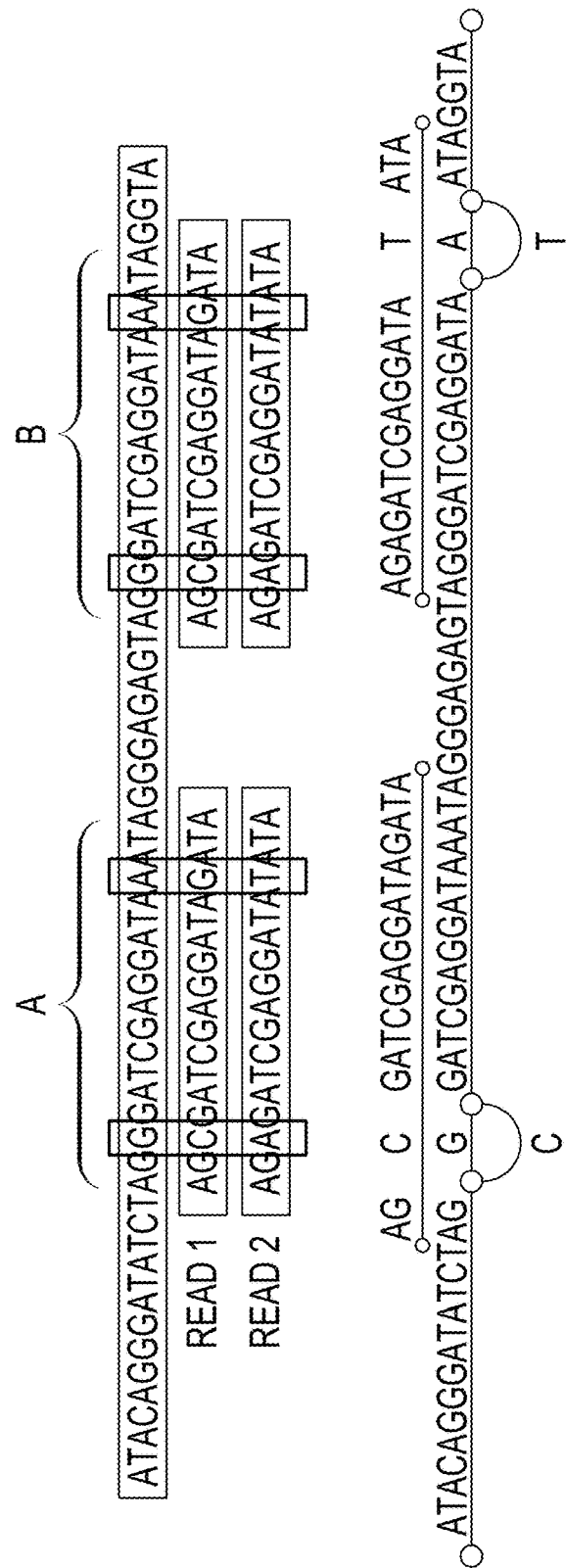
FIG. 18 illustrates two reads (read 1 set forth as SEQ ID NO:11 and read 2 set forth as SEQ ID NO:12) being mapped to the linear reference genome (SEQ ID NO:13) (top) and the same reads mapped to a GGM representation that includes SNP information (SEQ ID NO:14) (bottom).

Using the GGM approach described herein, a model of the human chromosome 21 was developed that incorporated all known single nucleotide variants, insertions and deletions. The computation pipeline used is depicted in FIG. 11 where the sprouts algorithm described above was used to construct the model of the human chromosome 21 using the linear reference sequence and mutation information. FIG. 12 shows a small part of the chromosome 21 GGM showing edges that represent basic mutations using single nucleotide polymorphism data obtained from dbSNP. In order to include structural mutations, data was collected from public repositories and using a basic reference GGM for the region, each mutation was passed through the sprouts algorithm to identify the affected subgraph and nodes and edges were inserted appropriately (FIG. 18).

Example 6

This example describes the determination of edge weightings within the graph using a probabilistic cost function that combines known information.

Figure 15A:
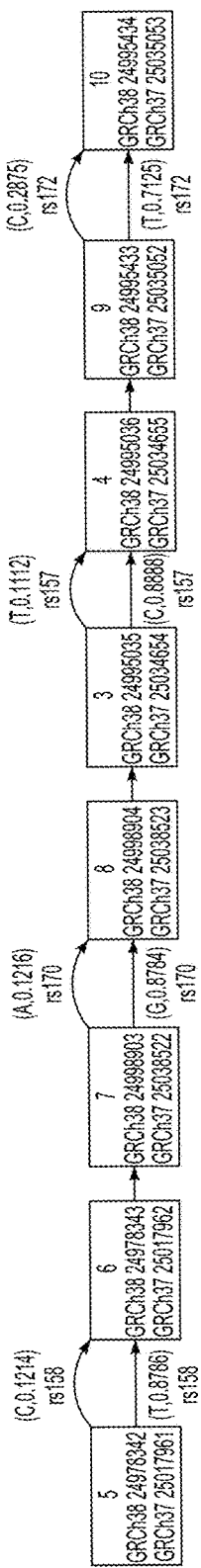
FIGS. 15A-15C illustrate the personalisation of a reference genome for a small section of chromosome 7 of the human genome. The super population is Europe and the subpopulation is Tuscans in Italy. The standard edge weights in FIGS. 15A-15C represent the global minor allele frequency. The indicated "red" edge weights introduced in FIG. 15B represent the allele frequencies for the European super population, as defined in the HapMap and 1000 genomes projects. The indicated "blue" edge weights introduced in FIG. 15C represent the allele frequencies for the Tuscan subpopulation, as defined in the HapMap and 1000 genomes projects.
Figure 15B:
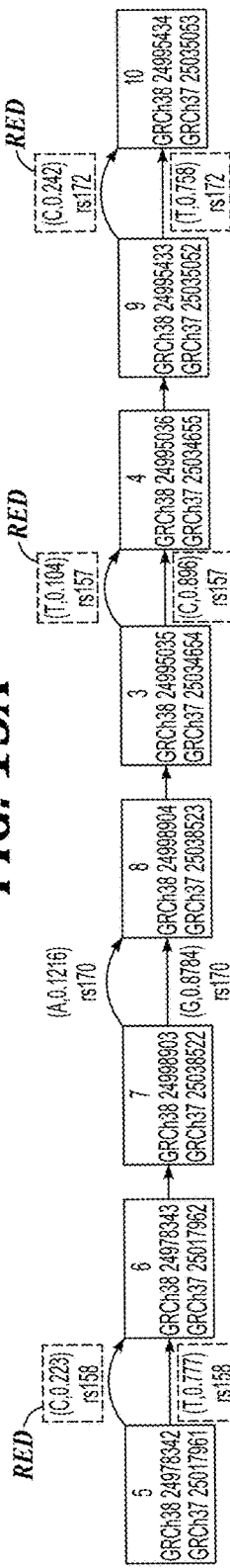
Figure 15C:
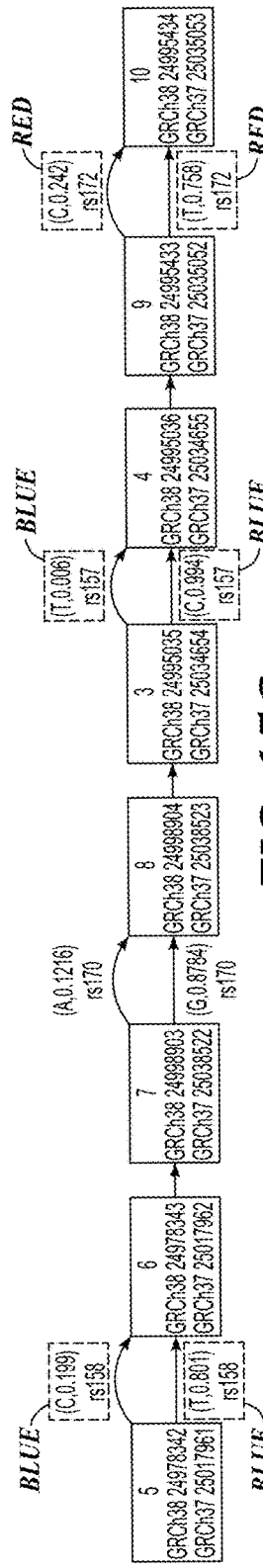
Figure 16:
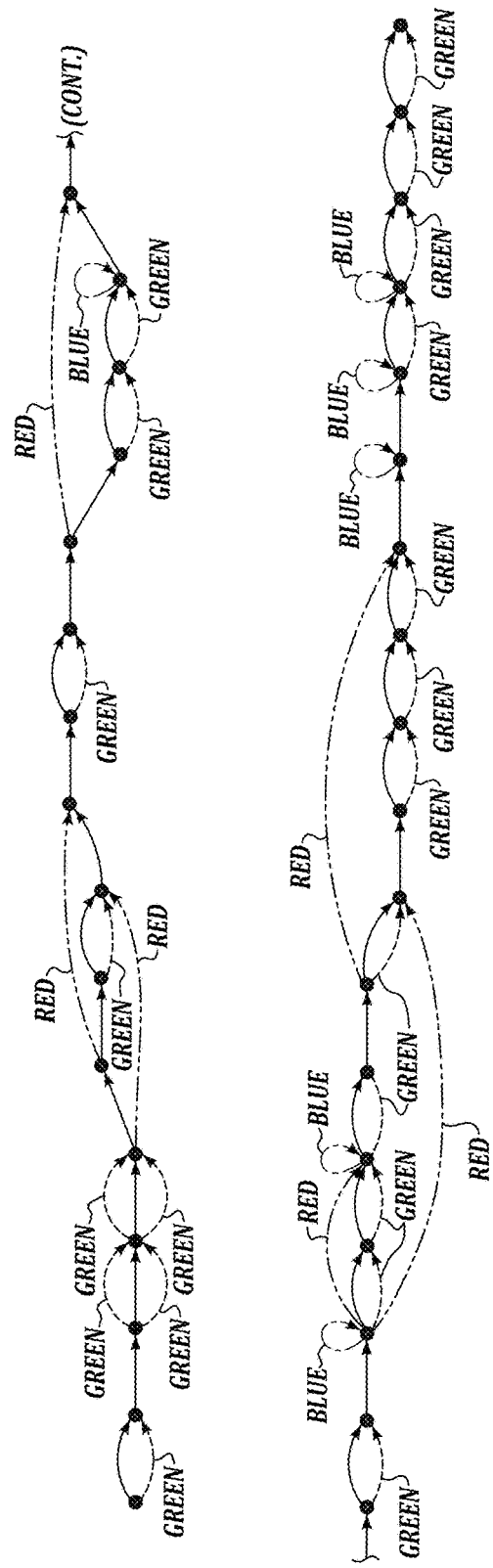
FIG. 16 illustrates part of BRCA2 reference (Chr 13: 32,340,400-32,340,455) generated with the GGM approach for basic mutations. Black edges represent the human reference genome, blue edges represent insertions, red edges represent deletions, and green edges represent SNV.

As shown in FIG. 11, the Sprouts algorithm is used to generate the reference GGM model and the CFgen (Cost Function generator) algorithm is used to calculate the probabilistic cost function. Multiple phenotypic datasets observed for an individual can be combined using CFGen to create edge weightings on a "personalised" reference GGM. For the initial implementation, the CFgen algorithm simply assigns edge weightings based on the minor allele frequencies of individual mutations as indicated in publically available databases, such as provided by the HapMap and 1000 genomes projects. The edge weightings represent the probability of observing that allele in a sample from the population of the "personalised" reference GGM model. FIG. 15 illustrates the personalization of a reference genome for a small section of the human chromosome 7. The graph shows four standard SNPs (i.e., with NCBI reference ids: rs158, rs170, rs157, rs172) found in both the most recent human reference genomes (the GRCH38 and GRCH37 co-ordinates are indicated in the node labels) that have population-specific allele frequencies given by the HapMap project. The edges between the start and end nodes for each mutation have 3 attributes: a sequence, a weighting, and a reference ID. The indicated sequence represents the allele for that mutation. The weighting is the observed frequency of that allele within a population and the reference ID is taken from the public database dbSNP. The sequences between the SNPs are not shown for ease of illustration as they are very long and contain other more complex mutations. The weights representing the global minor allele frequency are represented in FIG. 15A. The "red" edge weights introduced in FIG. 15B reflect the super population of Europe as defined in the HapMap and 1000 genomes projects. The "blue" edge weights introduced in FIG. 15C reflect the subpopulation of Tuscans in Italy as defined in the HapMap and 1000 genomes projects.

In the graph represented in FIG. 15A, only the global population is known and so all the edge weights are "black". In the middle graph the super population is known (i.e., Europe) and so where there is available information the edge weights are changed to those found in the super population. See FIG. 15B.

In FIG. 15C, the sub population is known (i.e., Tuscans in Italy) and, hence, for each SNP, available frequencies for the subpopulation are used as an edge weight. If there is no information for the defined sub-population but there is information for an applicable super population, then the frequency for the super population is used as the edge weight. If no information is available then the global allele frequency is used. If there is no information at any level for the allele, then the edge weightings for that mutation are either equally distributed or can be biased towards the reference allele. Thorough testing of population bias while using the GGM and the FEKs alignment algorithm will allow for the correct edge weightings to be generated.

The cost function generator algorithm can be expanded to include multiple input phenotypic datasets, such as GWAS, disease specific mutation rates, and error rates of sequencing technology. Using a training set, machine learning techniques can be generated to create a biased nonlinear function of all input information in order to weight the edges.

As addition to individual edge weightings, the GGM contains a sparse interaction matrix using meta information. This allows the GGM to be iteratively updated during read alignment or analysis. For example, if an allele is observed, then all linked alleles are given an increased weighting to reflect that the alleles are frequently observed together. The meta information incorporated into the model can include information related to genome-wide association studies, phenotype information, phasing information, parental genetic information, linkage equilibrium, and the like.

Example 7

This example describes an illustrative use of meta-information to define interactions between nodes and edges in the GGM.

Meta-information can include, but is not limited to: genome wide association studies (GWAS), phenotype information, phasing information, parental genetic information, and linkage disequilibrium information. In addition to generated individual edge weightings, the GGM can contain a sparse interaction matrix using meta-information. This allows the GGM to be iteratively updated during read alignment or analysis. If an allele is observed, then all linked alleles are given an increased weighting to reflect that the alleles are frequently observed together.

Figure 17A:
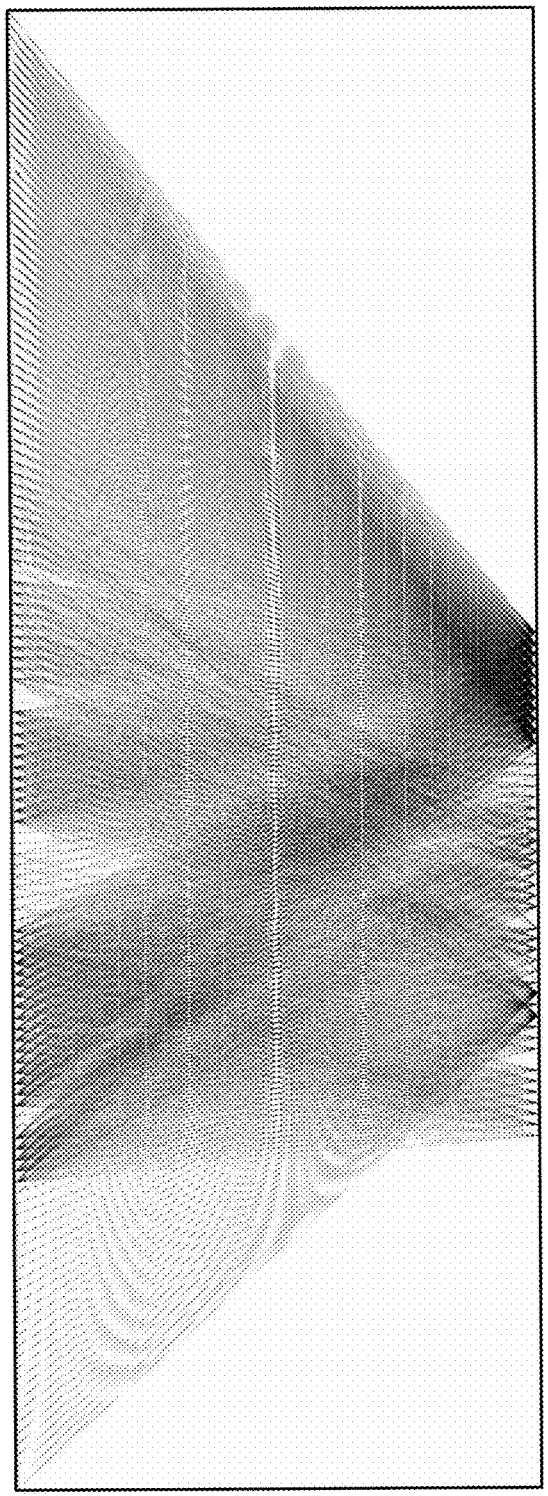
FIG. 17A illustrates the genotype-to-phenotype links for BRCA2 (Chr 13: 32, 340, 400-32, 340, 455).
Figure 17B:
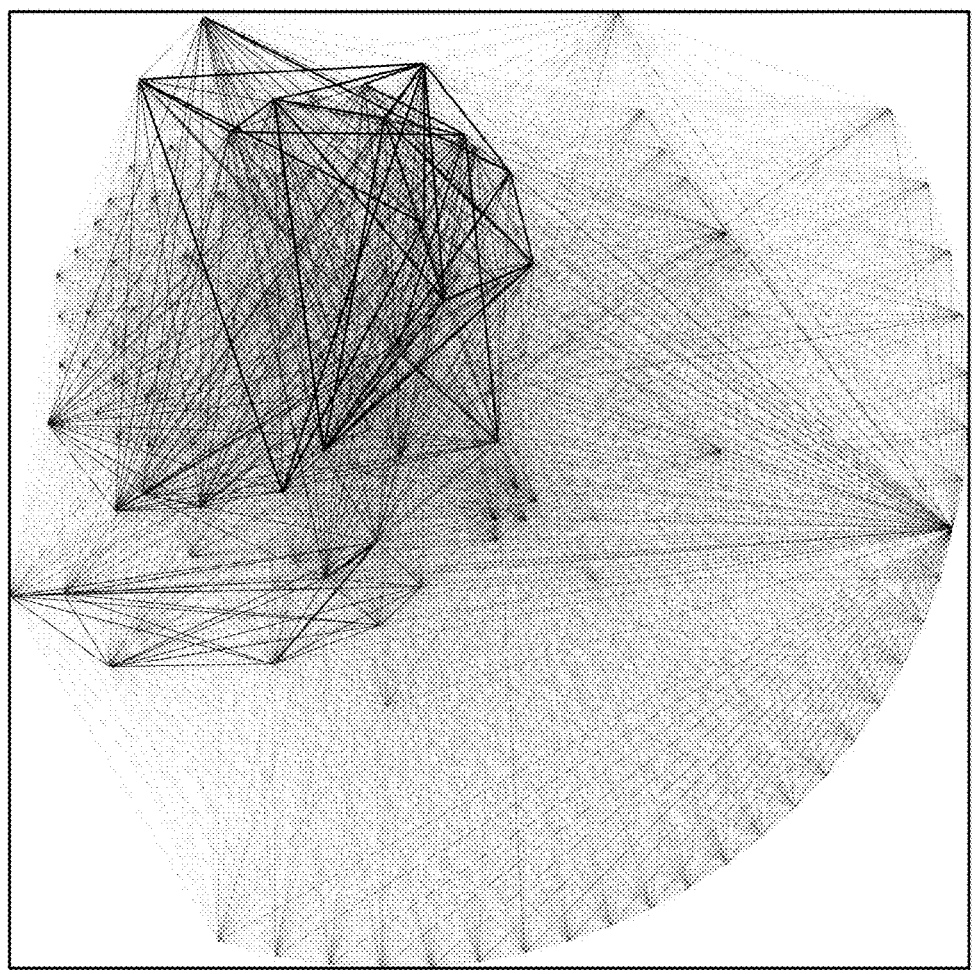
FIG. 17B illustrates the meta-graph linking genotypes based on shared phenotypes where the edge thickness correlates to the number of shared phenotypes.

As shown in FIGS. 17A and 17B, a full implementation of the GNOmics Database and Sprouts algorithm exists for the BRCA2 gene with meta-information from mutations associated with the diseased gene. Specifically, FIG. 17A illustrates the genotype-to-phenotype links for BRCA2 (Chr 13: 32,340,400-32,340,455), whereas FIG. 17B illustrates the meta-graph linking genotypes based on shared phenotypes where the edge thickness correlates to the number of shared phenotypes.

Example 8

This example describes performing alignments of individual reads from a read sequence to a reference GGM to find the optimal combined alignment of the set of sequences.

Traditional read alignment algorithms treat single or paired reads generated from sequencing machines individually and find the optimal alignment for each individual read (or paired reads). In contrast, the GGM approach uses a FEKs (fixed edge k-mers) algorithm. The read alignment is performed iteratively using subsets of the set of the input reads, which are also referred to in aggregate as the read pool. Also, unlike existing methods that index the reference graph and use the read to search within the index, the GGM FEKs algorithm searches for GGM fixed edge k-mers (FEK) within members of the indexed read pool.

Figure 13A:
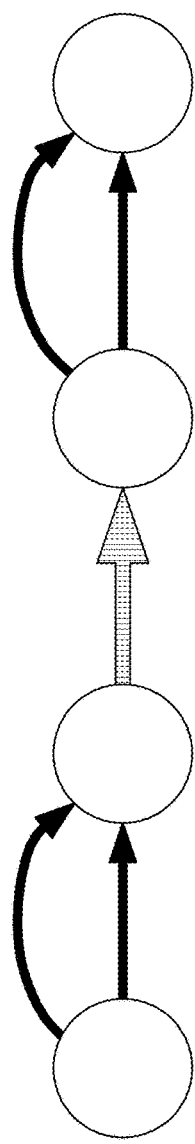
FIGS. 13A and 13B illustrate fixed edge k-mers (FEK). A FEK is a bridge between two nodes within the personalised reference GGM, which if removed results in a disjointed graph. A bridge is a path that connects a node having no more than one outgoing edge to a node having no more than one incoming edge.

An edge k-mers (FEK) is defined as a bridge between two nodes within the personalised reference GGM, where removal of the bridge would result in breaking or disjoining of the graph. For example, the hashed edge in FIG. 13A is a FEK (or "bridge") because the graph disjoint if it were removed from the graph. A subset of the read pool is generated with the individual reads that contain (or partially contain) the FEK sequence. A single read can be placed in multiple subsets as the subsets are not disjoint. For each subset, a local alignment is performed and scored for each read in the subset to generate a set of read-FEK pair (or "read-bridge pair") scores. The scoring process in the algorithm can be performed for each subset in parallel to enhance efficiency and speed. Once all read-FEK pair scores are calculated, they are combined in a matrix and using the meta-information interaction values, the best combination of placements is chosen for the reads contained within all the read pools. Any suitable technique may be used to determine the best combination of placements of the reads using the matrix, including but not limited to an eigenvalue decomposition, a spectral mapping, and a functional analysis using Hilbert or Banach spaces. Any single read can only be assigned to a single reference FEK, although any one FEK can have multiple reads from the read pool assigned to it.

Figure 13B:
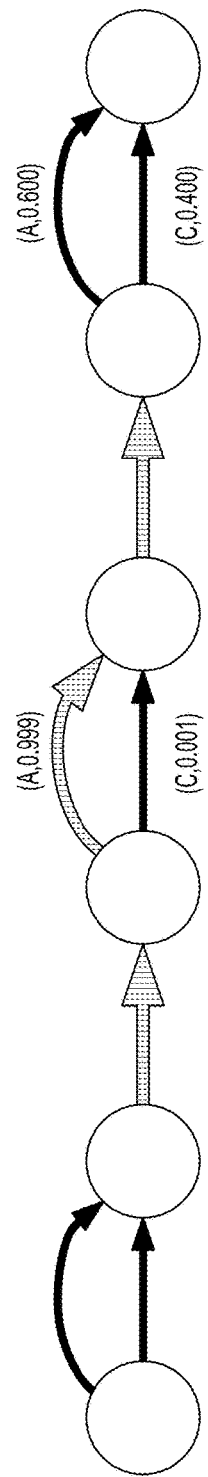

Once the reads are aligned to the graph, contradictory edges and superfluous edges are pruned from the reference GGM. The process is repeated using new FEKs that may arise after the pruning state. Additionally, highly probable FEKs, where the FEK is a bridge containing an edge with a weight above a defined threshold, can also be used. As shown in FIG. 13B, the three hashed edges are merged and considered to be a highly probable FEK in the second stage of the alignment in view of the high weight assigned to the A SNP between the $3^{rd}$ and $4^{th}$ nodes. After each stage, a new set of highly probable FEKs is generated from the previously pruned GGM and the threshold for a qualifying highly probably FEK can be lowered to generate larger subsets.

The FEKs algorithm is an iterative algorithm that can be optimised for less powerful computers using mass parallelisation when calculating scores for each stage. The algorithm ends when the subsets are too small for combined alignment. At such a point, each remaining, unassigned read is treated as a subsequence to be found in the GGM.

For a specific individual's genome, the GGM is generated and the reference graph is iteratively pruned using FEKs as seed points for tracing the most probable path. The meta-information interaction matrix can be used to update the edge weights as the seeded paths are generated. If an edge with known interactions is selected due to the alignment of reads, the weights of associated edges that have not been traced are recalculated to include a weighting representing a correlation between the two edges.

Using the GGM as a reference structure onto which reads are aligned provides many benefits over the current linear text reference structures. The GGM holds extensive amounts of known data about common and rare variants. This means that if two alleles are almost as likely at a particular position (e.g., where the major allele is present in 51% and the minor allele in 49% of a population), then the GGM could still align to the less common form (i.e., minor allele) perfectly at that position, whereas a linear reference would have indicated a mismatch.

Moreover, the GGM can be used to represent a customised reference genome, which allows the edge weightings to be differently customised between populations. In contrast, a linear reference genome imposes significant bias towards the reference used. Accordingly, there is likely to be a significant reduction in bias towards the reference used during alignment of individuals from two separate populations to a personalised reference GGM.

When performing an alignment using the FEKs algorithm, not only is a plethora of known variants being considered within the reference model, but an alignment of multiple reads is being performed simultaneously rather than treating each read (or read pair) sequentially as an independent entity. For example, the top of FIG. 19 illustrates an alignment to a linear reference where two reads treated independently both map to positions A and B with equal likelihood due to two mismatches. However, when considered together on a GGM reference (see bottom of FIG. 19), read 1 maps to position A and read 2 maps to position B because the GGM contains additional information of a minor SNP alleles that are matched differently by the reads. Therefore, each read is treated as a partial match to the corresponding minor allele rather than an outright mismatch.

Example 9

This example describes phasing using the GGM approach.

Phasing is the process of determining the two allele sequences from the unordered combination of genotypes at each site. When approaching the problem from graph theory point of view, there is an easy transition from tracing one path through the graph representation of an individual's genome to tracing two paths. While the GGM approach works from this basic concept, it differs significantly from other algorithms through the use of the meta-graph and read depth to predict the alleles within particular subgraphs and edges in the GGM of an individual's genome once the alignment is complete.

Personalised reference GGMs are created for each parent using either phenotype information or aligned sequence information. At places in the child's genome where there are homozygous mutations, the SNPs can be used as seeds for the parental reference GGMs. The seeds are used to prune the parental reference GGMs by taking into consideration the meta-graph of linked edge information. This iterative process allows the parental reference GGMs to be reduced in complexity because highly unlikely or impossible edges are pruned. After seeding the parental reference genome, the process is reversed using homozygous positions in the parental genomes to seed into the child's genome. Statistical inferences can be made using the edge weightings of the parental graphs to determine which allele is more likely to have come from which parent in the diploid GGM representation of the child.

This technique is particularly effective in cases where the parents are from different populations with different phenotypes and, hence, the parents' reference GGMs will differ more significantly than if they are from the same population.

Example 10

This example describes variant discovery.

Variant calling is a natural second stage of the FEKs algorithm. When aligning the reads an individual's GGM representation of their genome will be created and new edges will be added to the GGM when a variant not observed in the initial personalised reference GGM is discovered in the individual.

Further Examples

Further illustrative, non-exclusive examples of descriptions of some methods and systems in accordance with the scope of the present disclosure are presented in the following numbered paragraphs. The following paragraphs are not intended to be an exhaustive set of descriptions, and are not intended to define minimum or maximum scopes, or required elements or steps, of the present disclosure. Rather, the numbered paragraphs are provided as illustrative examples of selected methods and systems that are within the scope of the present disclosure, with other descriptions of broader or narrower scopes, or combinations thereof, not specifically listed herein still being within the scope of the present disclosure.

X1. A computer-implemented method for updating a graph that represents a portion of a reference genome, wherein each node of the graph includes a sequence position, and wherein edges of the graph include sequences of characters from a genomic alphabet, the method comprising:

obtaining a mutation record that includes one or more mutation sequences beginning at a mutation sequence start position and ending at a mutation sequence end position;

identifying a minimal spanning graph within the graph that includes the sequence positions between the mutation sequence start position and the mutation sequence end position;

determining a mutation start node within the minimal spanning graph at the mutation sequence start position and a mutation end node within the minimal spanning graph at the mutation sequence end position;

identifying one or more paths beginning at the mutation start node and ending at the mutation end node;

for each path of the one or more paths:
for each first node and second node within the path connected to each other by at least one edge, and for each mutation sequence of the one or more mutation sequences:
in response to determining that no existing edge between the first node and the second node includes a portion of the mutation sequence between the sequence position of the first node and the sequence position of the second node:
creating a new edge connecting the first node to the second node; and
adding a portion of the mutation sequence between the sequence position of the first node and the sequence position of the second node to the new edge;

removing any contradictory edges or superfluous edges from the graph after adding the new edges; and storing the updated edges and nodes in a graph data store.

X2. The method of Example X1, further comprising determining the mutation sequence start position and the mutation sequence end position using sequence position information in the mutation record or using flanking sequence information.

X3. The method of Example X1, wherein the genomic alphabet represents DNA nucleotides, RNA nucleotides, or protein amino acids.

X4. The method of Example X1, wherein creating the new edge connecting the first node to the second node includes adding a probability value to the new edge based on probability information within the mutation record.

X5. The method of Example X4, wherein creating the new edge connecting the first node to the second node further includes updating probability values of other edges connecting the first node and the second node to account for the probability value added to the new edge.

X6. The method of Example X4, wherein the probability values are associated with population information.

X7. The method of Example X6, wherein populations are organized into a hierarchy that includes a global population, a set of super populations, and a set of sub populations.

X8. The method of Example X6, wherein populations indicate separate phenotypic groups.

X9. The method of Example X8, wherein a phenotypic group includes subjects identified as possessing or having an increased probability of possessing a common trait, feature, symptom, disease, or condition.

X10. The method of Example X1, wherein edges of the graph include identifiers for locating a particular sequence in a public data repository.

X11. The method of Example X10, wherein the identifiers are Reference SNP cluster IDs (rs numbers), European Bioinformatics Institute (EBI) structural variant numbers (esv numbers), or National Center for Biotechnology Information (NCBI) structural variant numbers (nsv numbers).

X12. The method of Example X1, wherein groups of edges in the graph are associated in a correlation data store.

X13. The method of Example X12, wherein creating the new edge connecting the first node to the second node includes updating associations in the correlation data store that are affected by the creation of the new edge.

X14. The method of Example X12, wherein removing any contradictory edges or superfluous edges from the graph after adding the new edges includes updating associations in the correlation data store that are affected by the removal of the contradictory edges or the superfluous edges.

X15. The method of Example X1, wherein the mutation start node and the mutation end node are the same node.

X16. The method of Example X15, wherein the new edge includes a value indicating a number of repetitions of the sequence of the new edge.

X17. The method of Example X1, wherein the sequence of the new edge contains zero characters.

X18. The method of Example X1, wherein each edge is directed, and wherein traversing an edge in reverse of its direction causes the sequence of the edge to be interpreted as a reverse complement of the sequence.

X19. The method of Example X1, wherein the minimal spanning graph begins at a spanning graph start node and ends at a spanning graph end node, and wherein determining the mutation start node within the minimal spanning graph at the mutation sequence start position includes:

determining that no node exists within the minimal spanning graph at the mutation sequence start position;

creating a new node for the mutation start node, wherein the sequence position of the new node is the mutation sequence start position.

X20. The method of Example X19, wherein the sequence position of the new node is between a sequence position of a region of interest start node and a sequence position of a region of interest end node, wherein a subgraph between the region of interest start node and the region of interest end node includes all paths that include the mutation sequence start position, wherein the region of interest start node and the region of interest end node are connected by one or more paths, wherein each path includes a path sequence defined by the sequences of edges within the path, and wherein the method further comprises, for each path having a path sequence with a length greater than zero:

creating a first edge from a node before the mutation sequence start position on a path starting at the region of interest start node to the new node;

adding a sequence to the first edge that includes a portion of the path sequence between the sequence position of the region of interest start node and the mutation sequence start position;

creating a second edge from the new node to a node after the mutation sequence start position on a path ending at the region of interest end node; and adding a sequence to the second edge that includes a portion of the path sequence between the mutation sequence start position and the sequence position of the region of interest end node.

X21. The method of Example X20, further comprising removing the edges of the paths having path sequences with a length greater than zero that do not pass through the new node.

X22. The method of Example X20, further comprising adding probability values to the first edge and the second edge based on probability values of the edges of the path.

X23. The method of Example X1, wherein the minimal spanning graph begins at a spanning graph start node and ends at a spanning graph end node, and wherein determining the mutation end node within the minimal spanning graph at the mutation sequence end position includes:

determining that no node exists within the minimal spanning graph at the mutation sequence end position;

creating a new node for the mutation end node, wherein the sequence position of the new node is the mutation sequence end position.

X24. The method of Example X23, wherein the sequence position of the new node is between a sequence position of a region of interest start node and a sequence position of a region of interest end node, wherein a subgraph between the region of interest start node and the region of interest end node includes all paths that include the mutation sequence end position, wherein the region of interest start node and the region of interest end node are connected by one or more paths, wherein each path includes a path sequence defined by the sequences of edges within the path, and wherein the method further comprises, for each path having a path sequence with a length greater than zero:

creating a first edge from a node before the mutation sequence end position on a path starting at the region of interest start node to the new node;

adding a sequence to the first edge that includes a portion of the path sequence between the sequence position of the region of interest start node and the mutation sequence end position;

creating a second edge from the new node to a node after the mutation sequence end position on a path ending at the region of interest end node; and adding a sequence to the second edge that includes a portion of the path sequence between the mutation sequence end position and the sequence position of the region of interest end node.

X25. The method of Example X23, further comprising removing the edges of the paths having path sequences with a length greater than zero that do not pass through the new node.

X26. The method of Example X23, further comprising adding probability values to the first edge and the second edge based on probability values of the edges of the path.

X27. The method of Example X1, further comprising:

obtaining a plurality of mutation records; and subdividing the plurality of mutation records into disjoint subsets that have no overlap between the affected sequence locations.

X28. The method of Example X27, further comprising concurrently processing mutation records from the disjoint subsets.

X29. The method of Example X27, further comprising subdividing the plurality of mutation records into mutation types by linearity or complexity.

X30. A computer-implemented method of aligning reads of a read sequence to a graph that represents a genome and polymorphisms therein, wherein the graph includes a plurality of edges, the method comprising:
  selecting a set of bridges from the graph;
  for each bridge in the set of bridges:
    selecting a subset of a read pool, wherein reads in the subset contain at least a portion of the bridge; and
    for each read in the subset:
      performing a local alignment for the read;
      scoring the local alignment for the read to generate a read-bridge pair score; and
      inserting the read-bridge pair score into a score matrix;
  using the score matrix to determine a best combination of placements of reads for the set of bridges; and
    placing the reads on the graph.

X31. The method of Example X30, wherein selecting the set of bridges from the graph includes selecting at least one edge from the graph that connects a node having no more than one outgoing edge to a node having no more than one incoming edge.

X32. The method of Example X31, further comprising selecting a subsequent set of bridges from the graph.

X33. The method of Example X32, further comprising pruning contradictory edges and superfluous edges from the graph before selecting a subsequent set of bridges from the graph.

X34. The method of Example X32, wherein selecting at least one edge from the graph includes selecting at least one edge from the graph having a probability greater than a confidence threshold;
  wherein selecting a subsequent set of bridges from the graph includes selecting at least one subsequent edge from the graph that connects a node having no more than one outgoing edge to a node having no more than one incoming edge; and
  wherein selecting the at least one subsequent edge from the graph includes selecting at least one subsequent edge from the graph having a probability greater than a lower confidence threshold compared to the confidence threshold.

X35. The method of Example X34, further comprising retrieving probability information for the edges based on phenotypic information.

X36. The method of Example X35, wherein the phenotypic information is determined based on a population.

X37. The method of Example X35, wherein the local alignment is based on the probability information.

X38. The method of Example X30, wherein the local alignment is based on information regarding the quality of the read.

X39. The method of Example X30, wherein the local alignment is based on information in a correlation table.

X40. The method of Example X39, wherein the information in the correlation table includes associations and co-occurrence scores for one or more of genes, alleles, and mutations.

X41. The method of Example X34, further comprising updating probabilities in the graph based on information in a correlation table.

X42. The method of Example X30, further comprising updating information within a correlation table based on the placement of the reads on the graph.

X43. The method of Example X30, wherein the local alignment is performed using a Smith-waterman algorithm, dynamic programming, or position-specific scoring matrices.

X44. The method of Example X30, wherein using the score matrix to determine a best combination of placements of reads for the set of bridges includes performing an eigenvalue decomposition, a spectral mapping, or a functional analysis using Hilbert or Banach spaces.

X45. A system for generating graphs based on reference genome information, the system comprising:
  a graph data store configured to store a plurality of edge records, wherein each edge record includes a start node, an end node, a sequence listing, and a probability value; and
  at least one computing device configured to:
    obtain mutation records representing polymorphisms within the reference genome; and
    create and modify edge records within the graph data store based on the mutation records.

X46. The system of Example X45, further comprising a correlation data store configured to store a plurality of correlation records, wherein each correlation record indicates a probability of a second edge being present given the presence of a first edge.

X47. The system of Example X45, wherein each edge record includes an indication of a population.

X48. The system of Example X45, wherein at least one edge record includes a start node and an end node that are the same.

X49. The system of Example X48, wherein the at least one edge record that includes a start node and an end node that are the same also includes a value indicating a number of repetitions.

X50. A system for performing read alignments to a graph that represents a genome and polymorphisms therein, the system comprising:
  a graph data store configured to store information representing the graph, the information including a plurality of edge records;
  at least one bridge computing device configured to:
    receive a read pool;
    select a set of bridges from the edge records stored in the graph data store;
    for each bridge in the set of bridges:
      select a subset of the read pool, wherein reads in the subset contain at least a portion of the bridge; and
      transmit reads from the subset of the read pool and the bridge to an alignment computing device;
  a plurality of alignment computing devices each configured to:
    receive one or more reads and a bridge with which the reads are associated;
    perform a local alignment for each of the one or more reads;
    score the local alignment for each of the one or more reads to generate a read-bridge pair score for each of the one or more reads; and
    transmit the read-bridge pair scores to a matrix processing computing device; and
  at least one matrix processing computing device configured to:
    receive read-bridge pair scores from the plurality of alignment computing devices;
    insert the read-bridge pair scores into a score matrix;
    use the score matrix to determine a best combination of placements of reads for the set of bridges; and
    place the reads on the graph.

X51. The system of Example X50, wherein selecting the set of bridges from the graph includes selecting at least one edge from the graph that connects a node having no more than one outgoing edge to a node having no more than one incoming edge.

X52. The system of Example X50, further comprising a correlation data store configured to store a plurality of correlation records, wherein each correlation record indicates a probability of a second edge being present given the presence of a first edge.

X53. The system of Example X52, wherein performing the local alignment is based on the correlation records from the correlation data store.

X54. The system of Example X52, wherein placing the reads on the graph further includes updating information within the correlation data store based on the placement of the reads on the graph.

X55. The system of Example X50, further comprising a computing device configured to present a personalization interface, wherein the personalization interface is configured to:
  receive an indication of a phenotypic group; and
  prune the graph to exclude edges from consideration for alignment that are not likely to be found within the phenotypic group.

X56. The system of Example X50, wherein the graph includes a plurality of edges, and wherein each edge includes sequence information.

X57. The system of Example X50, wherein the local alignment is performed using a Smith-waterman algorithm, dynamic programming, or position-specific scoring matrices.

X58. The method of Example X50, wherein using the score matrix to determine a best combination of placements of reads for the set of bridges includes performing an eigenvalue decomposition, a spectral mapping, or a functional analysis using Hilbert or Banach spaces.

While illustrative embodiments have been illustrated and described, it will be appreciated that various changes can be made therein without departing from the spirit and scope of the invention.

The embodiments of the invention in which an exclusive property or privilege is claimed are defined as follows:

1. A computer-implemented method for updating a graph that represents a portion of a reference genome, wherein each node of the graph includes a sequence position, and wherein edges of the graph include sequences of characters from a genomic alphabet, the method comprising:
   obtaining a mutation record that includes one or more mutation sequences beginning at a mutation sequence start position and ending at a mutation sequence end position;
   identifying a minimal spanning graph within the graph that includes the sequence positions between the mutation sequence start position and the mutation sequence end position;
   for each mutation sequence of the one or more mutation sequences:
   determining a linearity of the mutation sequence with respect to a node ordering, wherein the linearity is linear, semi-linear, backward semi-linear, forward semi-linear, or non-linear,
   wherein a linear mutation is a mutation represented by a single directed edge between two adjacent ordered nodes or homeomorphic representations thereof,
   wherein a semi-linear mutation is a mutation represented by multiple forward directed edges between adjacent ascending nodes or homeomorphic representations thereof,
   wherein a forward semi-linear mutation is a mutation represented by multiple forward edges between a node and two or more higher nodes or homeomorphic representations thereof, wherein a backward semi-linear mutation is a mutation represented by multiple forward edges between two or more lower nodes and a node or homeomorphic representations thereof, and wherein a non-linear mutation is a mutation represented by at least one of:

multiple forward and backward edges between two or more nodes or homeomorphic representations thereof, and one or more forward edges beginning and ending at the same node or homeomorphic representations thereof;

determining a mutation start node within the minimal spanning graph at the mutation sequence start position and a mutation end node within the minimal spanning graph at the mutation sequence end position using information obtained from the determined linearity of the mutation sequence;

identifying one or more paths beginning at the mutation start node and ending at the mutation end node;

for each path of the one or more paths:

for each first node and second node within the path connected to each other by at least one edge:

in response to determining that no existing edge between the first node and the second node includes a portion of the mutation sequence between the sequence position of the first node and the sequence position of the second node:

creating a new edge connecting the first node to the second node; and adding a portion of the mutation sequence between the sequence position of the first node and the sequence position of the second node to the new edge;

removing any contradictory edges or superfluous edges from the graph after adding the new edges; and storing the updated edges and nodes in a graph data store.

2. The method of claim 1, wherein the genomic alphabet represents DNA nucleotides, RNA nucleotides, or protein amino acids.

3. The method of claim 1, wherein creating the new edge connecting the first node to the second node includes adding a probability value to the new edge based on probability information within the mutation record.

4. The method of claim 3, wherein creating the new edge connecting the first node to the second node further includes updating probability values of other edges connecting the first node and the second node to account for the probability value added to the new edge.

5. The method of claim 3, wherein the probability values are associated with population information.

6. The method of claim 5, wherein populations are organized into a hierarchy that includes a global population, a set of super populations, and a set of sub populations.

7. The method of claim 5, wherein populations indicate separate phenotypic groups.

8. The method of claim 7, wherein a phenotypic group includes subjects identified as possessing or having an increased probability of possessing a common trait, feature, symptom, disease, or condition.

9. The method of claim 1, wherein edges of the graph include identifiers for locating a particular sequence in a public data repository.

10. The method of claim 9, wherein the identifiers are Reference SNP cluster IDs (rs numbers), European Bioinformatics Institute (EBI) structural variant numbers (esv numbers), or National Center for Biotechnology Information (NCBI) structural variant numbers (nsv numbers).

11. The method of claim 1, wherein groups of edges in the graph are associated in a correlation data store.

12. The method of claim 11, wherein creating the new edge connecting the first node to the second node includes updating associations in the correlation data store that are affected by the creation of the new edge.

13. The method of claim 11, wherein removing any contradictory edges or superfluous edges from the graph after adding the new edges includes updating associations in the correlation data store that are affected by the removal of the contradictory edges or the superfluous edges.

14. The method of claim 1, wherein the mutation start node and the mutation end node are the same node.

15. The method of claim 14, wherein the new edge includes a value indicating a number of repetitions of the sequence of the new edge.

16. The method of claim 1, wherein the sequence of the new edge contains zero characters.

17. The method of claim 1, wherein each edge is directed, and wherein traversing an edge in reverse of its direction causes the sequence of the edge to be interpreted as a reverse complement of the sequence.

18. The method of claim 1, wherein the minimal spanning graph begins at a spanning graph start node and ends at a spanning graph end node, and wherein determining the mutation start node within the minimal spanning graph at the mutation sequence start position includes:

determining that no node exists within the minimal spanning graph at the mutation sequence start position;

creating a new node for the mutation start node, wherein the sequence position of the new node is the mutation sequence start position.

19. The method of claim 18, wherein the sequence position of the new node is between a sequence position of a region of interest start node and a sequence position of a region of interest end node, wherein a subgraph between the region of interest start node and the region of interest end node includes all paths that include the mutation sequence start position, wherein the region of interest start node and the region of interest end node are connected by one or more paths, wherein each path includes a path sequence defined by the sequences of edges within the path, and wherein the method further comprises, for each path having a path sequence with a length greater than zero:

creating a first edge from a node before the mutation sequence start position on a path starting at the region of interest start node to the new node;

adding a sequence to the first edge that includes a portion of the path sequence between the sequence position of the region of interest start node and the mutation sequence start position;

creating a second edge from the new node to a node after the mutation sequence start position on a path ending at the region of interest end node; and adding a sequence to the second edge that includes a portion of the path sequence between the mutation sequence start position and the sequence position of the region of interest end node.

20. The method of claim 19, further comprising removing the edges of the paths having path sequences with a length greater than zero that do not pass through the new node.

21. The method of claim 19, further comprising adding probability values to the first edge and the second edge based on probability values of the edges of the path.

22. The method of claim 1, wherein the minimal spanning graph begins at a spanning graph start node and ends at a spanning graph end node, and wherein determining the mutation end node within the minimal spanning graph at the mutation sequence end position includes:
   determining that no node exists within the minimal spanning graph at the mutation sequence end position;
   creating a new node for the mutation end node, wherein the sequence position of the new node is the mutation sequence end position.

23. The method of claim 22, wherein the sequence position of the new node is between a sequence position of a region of interest start node and a sequence position of a region of interest end node, wherein a subgraph between the region of interest start node and the region of interest end node includes all paths that include the mutation sequence end position, wherein the region of interest start node and the region of interest end node are connected by one or more paths, wherein each path includes a path sequence defined by the sequences of edges within the path, and wherein the method further comprises, for each path having a path sequence with a length greater than zero:
   creating a first edge from a node before the mutation sequence end position on a path starting at the region of interest start node to the new node;
   adding a sequence to the first edge that includes a portion of the path sequence between the sequence position of the region of interest start node and the mutation sequence end position;
   creating a second edge from the new node to a node after the mutation sequence end position on a path ending at the region of interest end node; and
   adding a sequence to the second edge that includes a portion of the path sequence between the mutation sequence end position and the sequence position of the region of interest end node.

24. The method of claim 22, further comprising removing the edges of the paths having path sequences with a length greater than zero that do not pass through the new node.

25. The method of claim 22, further comprising adding probability values to the first edge and the second edge based on probability values of the edges of the path.

26. The method of claim 1, further comprising:
   obtaining a plurality of mutation records, wherein each mutation record includes a mutation sequence start position and a mutation sequence end position; and
   subdividing the plurality of mutation records into disjoint subsets that have no overlap between affected sequence locations indicated by the mutation sequence start positions and the mutation sequence end positions of the mutation records.

27. The method of claim 26, further comprising concurrently processing mutation records from the disjoint subsets.

28. The method of claim 26, further comprising subdividing the plurality of mutation records into mutation types by linearity or complexity.

29. A system for generating graphs based on reference genome information, the system comprising:
   a graph data store configured to store a plurality of edge records, wherein each edge record includes a start node having a sequence start position, an end node having a sequence end position, a sequence listing, and a probability value; and
   at least one computing device configured to:
      obtain mutation records representing polymorphisms within the reference genome; and
      create and modify edge records within the graph data store based on the mutation records;
   wherein each mutation record includes one or more mutation sequences beginning at a mutation sequence start position and ending at a mutation sequence end position; and
   wherein creating and modifying edge records includes:
      identifying a minimal spanning graph within the plurality of edge records that includes sequence positions between the mutation sequence start position of a mutation record and the mutation sequence end position of the mutation record; and, for each mutation sequence of the one or more mutation sequences of the mutation record:
         determining a linearity of the mutation sequence with respect to a node ordering, wherein the linearity is linear, semi-linear, backward semi-linear, forward semi-linear, or non-linear,
            wherein a linear mutation is a mutation represented by a single directed edge between two adjacent ordered nodes or homeomorphic representations thereof,
            wherein a semi-linear mutation is a mutation represented by multiple forward directed edges between adjacent ascending nodes or homeomorphic representations thereof,
            wherein a forward semi-linear mutation is a mutation represented by multiple forward edges between a node and two or more higher nodes or homeomorphic representations thereof,
            wherein a backward semi-linear mutation is a mutation represented by multiple forward edges between two or more lower nodes and a node or homeomorphic representations thereof, and
            wherein a non-linear mutation is a mutation represented by at least one of:
               multiple forward and backward edges between two or more nodes or homeomorphic representations thereof, and
               one or more forward edges beginning and ending at the same node or homeomorphic representations thereof; and
         determining a mutation start node within the minimal spanning graph at the mutation sequence start position and a mutation end node within the minimal spanning graph at the mutation sequence end position using information obtained from the determined linearity of the mutation sequence.

30. The system of claim 29, further comprising a correlation data store configured to store a plurality of correlation records, wherein each correlation record indicates a probability of a second edge being present given the presence of a first edge.

31. The system of claim 29, wherein each edge record includes an indication of a population.

32. The system of claim 29, wherein at least one edge record includes a start node and an end node that are the same.

33. The system of claim 32, wherein the at least one edge record that includes a start node and an end node that are the same also includes a value indicating a number of repetitions.

* * * * *

SEQUENCE LISTING

```
<160> NUMBER OF SEQ ID NOS: 14

<210> SEQ ID NO 1
<211> LENGTH: 12
<212> TYPE: DNA
<213> ORGANISM: Artificial Sequence
<220> FEATURE:
<223> OTHER INFORMATION: Synthetic

<400> SEQUENCE: 1
aagctactag ct                                                              12

<210> SEQ ID NO 2
<211> LENGTH: 18
<212> TYPE: DNA
<213> ORGANISM: Artificial Sequence
<220> FEATURE:
<223> OTHER INFORMATION: Synthetic

<400> SEQUENCE: 2
aagctagact aggaagct                                                        18

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
aagactccga ctgggacttt                                                      20

<210> SEQ ID NO 4
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: Wherein the N at position 12 can be G or C

<400> SEQUENCE: 4
gagcctggga tnaaa                                                           15

<210> SEQ ID NO 5
<211> LENGTH: 18
```

```
<212> TYPE: DNA
<213> ORGANISM: Artificial Sequence
<220> FEATURE:
<223> OTHER INFORMATION: Synthetic

<400> SEQUENCE: 5
atgaccgacg agatgaaa                                                    18

<210> SEQ ID NO 6
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: Wherein the N at position 12 can be G or A

<400> SEQUENCE: 6
atgaccgacg anatgaaa                                                    18

<210> SEQ ID NO 7
<211> LENGTH: 15
<212> TYPE: DNA
<213> ORGANISM: Artificial Sequence
<220> FEATURE:
<223> OTHER INFORMATION: Synthetic

<400> SEQUENCE: 7
atgaccgaca tgaaa                                                       15

<210> SEQ ID NO 8
<211> LENGTH: 27
<212> TYPE: DNA
<213> ORGANISM: Artificial Sequence
<220> FEATURE:
<223> OTHER INFORMATION: Synthetic

<400> SEQUENCE: 8
atgaccgacc gacgacgaga gatgaaa                                          27

<210> SEQ ID NO 9
<211> LENGTH: 17
<212> TYPE: DNA
<213> ORGANISM: Artificial Sequence
<220> FEATURE:
<223> OTHER INFORMATION: Synthetic

<400> SEQUENCE: 9
atggagatga aaaccga                                                     17

<210> SEQ ID NO 10
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: Wherein the N at position 15 can be G or C

<400> SEQUENCE: 10
atgaccgacg agatnaaa                                                    18

<210> SEQ ID NO 11
```

```
<211> LENGTH: 18
<212> TYPE: DNA
<213> ORGANISM: Artificial Sequence
<220> FEATURE:
<223> OTHER INFORMATION: Synthetic

<400> SEQUENCE: 11
agcgatcgag gatagata                                                   18

<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
agagatcgag gatatata                                                   18

<210> SEQ ID NO 13
<211> LENGTH: 62
<212> TYPE: DNA
<213> ORGANISM: Artificial Sequence
<220> FEATURE:
<223> OTHER INFORMATION: Synthetic

<400> SEQUENCE: 13
atacagggat atctagggat cgaggataaa tagggagagt agggatcgag gataaatagg     60
ta                                                                    62

<210> SEQ ID NO 14
<211> LENGTH: 62
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (17)..(17)
<223> OTHER INFORMATION: Wherein the N at posistion 17 can be G or C
<220> FEATURE:
<221> NAME/KEY: misc_feature
<222> LOCATION: (55)..(55)
<223> OTHER INFORMATION: Wherein the N at posistion 55 can be A or T

<400> SEQUENCE: 14
atacagggat atctagngat cgaggataaa tagggagagt agggatcgag gatanatagg     60
ta                                                                    62
```